(12) United States Patent
Milliman et al.

(10) Patent No.: US 8,348,122 B2
(45) Date of Patent: Jan. 8, 2013

(54) SURGICAL STAPLING DEVICE

(75) Inventors: Keith L. Milliman, Bethel, CT (US);
Bruce K. Jankowski, North Attleboro, MA (US); Douglas J. Cuny, Bethel, CT (US); Kevin Sniffin, Danbury, CT (US); Anthony Dato, East Haven, CT (US); Richard D. Gresham, Guilford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 1292 days.

(21) Appl. No.: 11/515,660

(22) Filed: Sep. 5, 2006

(65) Prior Publication Data

US 2007/0075117 A1 Apr. 5, 2007

Related U.S. Application Data

(60) Provisional application No. 60/714,141, filed on Sep. 2, 2005.

(51) Int. Cl.
*A61B 17/064* (2006.01)

(52) U.S. Cl. .............. 227/175.1; 227/175.2; 227/182.1

(58) Field of Classification Search ............... 227/175.1, 227/182.1, 178.1, 175.2
See application file for complete search history.

(56) References Cited

U.S. PATENT DOCUMENTS

| | | | |
|---|---|---|---|
| 3,388,847 A | 6/1968 | Kasulin et al. |
| 3,552,626 A | 1/1971 | Astafiev |
| 3,638,652 A | 2/1972 | Kelley |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |

(Continued)

FOREIGN PATENT DOCUMENTS

CA 908529 8/1972

(Continued)

*Primary Examiner* — Hemant M Desai
*Assistant Examiner* — Gloria R Weeks

(57) ABSTRACT

A surgical stapling device is disclosed for performing circular anastomoses. The surgical stapling device includes a handle portion, an elongated body portion and a head portion including an anvil assembly and a shell assembly. The head portion includes an anvil assembly including a tiltable anvil which will tilt automatically after the device has been fired and unapproximated. The tiltable anvil provides a reduced anvil profile to reduce trauma during removal of the device after the anastomoses procedure has been performed. The stapling device includes an approximation mechanism including a rotatable knob, a screw having a helical channel and an anvil retainer. The helical channel includes a dwell portion for providing a tactile indication to a surgeon that the anvil retainer has been advanced to a position wherein the anvil assembly can be removed from the anvil retainer. A removable trocar for attachment to the anvil assembly is also disclosed which includes a rib positioned proximally of a mounting projection. The rib is positioned to align the mounting projection with associated engagement structure of the anvil assembly.

20 Claims, 36 Drawing Sheets

U.S. PATENT DOCUMENTS

| | | | |
|---|---|---|---|
| 4,527,724 A | 7/1985 | Chow et al. | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,646,745 A | 3/1987 | Noiles | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,754,909 A | 7/1988 | Barker et al. | |
| 4,817,847 A | 4/1989 | Redtenbacher et al. | |
| 4,873,977 A | 10/1989 | Avant et al. | |
| 4,893,662 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,137,198 A * | 8/1992 | Nobis et al. | 227/175.3 |
| 5,139,156 A * | 8/1992 | Nakamura | 212/276 |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A * | 3/1993 | Gingold | 227/179.1 |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Bianco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A * | 8/1995 | Viola et al. | 227/179.1 |
| 5,445,644 A | 8/1995 | Pietrafitta et al. | |
| 5,447,514 A | 9/1995 | Gerry et al. | |
| 5,454,825 A | 10/1995 | Van Leeuwen et al. | |
| 5,470,006 A | 11/1995 | Rodak | |
| 5,474,223 A * | 12/1995 | Viola et al. | 227/179.1 |
| 5,497,934 A | 3/1996 | Brady et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,632,433 A * | 5/1997 | Grant et al. | 227/179.1 |
| 5,639,008 A * | 6/1997 | Gallagher et al. | 227/175.1 |
| 5,658,300 A | 8/1997 | Bito et al. | |
| 5,669,918 A * | 9/1997 | Balazs et al. | 606/139 |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,758,814 A | 6/1998 | Gallagher et al. | |
| 5,782,397 A * | 7/1998 | Koukline | 227/176.1 |
| 5,799,857 A | 9/1998 | Robertson et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,882,340 A | 3/1999 | Yoon | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,050,472 A | 4/2000 | Shibata | |
| 6,053,390 A | 4/2000 | Green et al. | |
| 6,066,145 A | 5/2000 | Wurster | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 * | 2/2001 | Bittner et al. | 227/180.1 |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balázs et al. | |
| 6,264,086 B1 | 7/2001 | McGuckin, Jr. | |
| 6,269,997 B1 | 8/2001 | Balázs et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,748 B1 | 8/2003 | Fung et al. | |
| 6,601,749 B2 | 8/2003 | Sullivan et al. | |
| 6,605,078 B2 | 8/2003 | Adams | |
| 6,623,227 B2 | 9/2003 | Scott et al. | |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |

| | | |
|---|---|---|
| 6,695,198 B2 | 2/2004 | Adams et al. |
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,945,444 B2 | 9/2005 | Gresham et al. |
| 6,981,941 B2 | 1/2006 | Whitman et al. |
| 7,032,798 B2 | 4/2006 | Whitman et al. |
| 7,059,331 B2 | 6/2006 | Adams et al. |
| 7,059,510 B2 | 6/2006 | Orban, III |
| 7,080,769 B2 | 7/2006 | Vresh et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,168,604 B2 * | 1/2007 | Milliman et al. .......... 227/176.1 |
| 7,179,267 B2 | 2/2007 | Nolan et al. |
| 7,182,239 B1 | 2/2007 | Myers |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0023325 A1 | 2/2005 | Gresham et al. |
| 2005/0051597 A1 | 3/2005 | Tolendano |
| 2005/0067454 A1 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0043148 A1 * | 3/2006 | Gresham et al. .......... 227/176.1 |
| 2006/0047307 A1 | 3/2006 | Ortiz et al. |
| 2006/0047308 A1 | 3/2006 | Ortiz et al. |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0241692 A1 | 10/2006 | McGuckin, Jr. et al. |
| 2006/0255090 A1 | 11/2006 | Milliman et al. |
| 2006/0289601 A1 | 12/2006 | Orban, III |
| 2007/0023475 A1 | 2/2007 | Csiky |
| 2007/0027473 A1 | 2/2007 | Vresh et al. |
| 2007/0029363 A1 | 2/2007 | Popov |
| 2007/0034666 A1 | 2/2007 | Holsten et al. |
| 2007/0034667 A1 | 2/2007 | Holsten et al. |
| 2007/0034668 A1 | 2/2007 | Holsten et al. |
| 2007/0038248 A1 | 2/2007 | Heinrch |
| 2007/0060952 A1 | 3/2007 | Roby et al. |

FOREIGN PATENT DOCUMENTS

| | | |
|---|---|---|
| DE | 1057729 | 5/1959 |
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0503689 | 9/1992 |
| FR | 1461464 | 12/1966 |
| FR | 1588250 | 4/1970 |
| FR | 2443239 | 12/1979 |
| GB | 1185292 | 3/1970 |
| GB | 2016991 | 9/1979 |
| GB | 2070499 | 9/1981 |
| NL | 7711347 | 10/1977 |
| WO | 8706448 | 11/1987 |
| WO | 8900406 | 1/1989 |
| WO | 9006085 | 6/1990 |
| WO | WO 02/080781 A2 | 10/2002 |

* cited by examiner

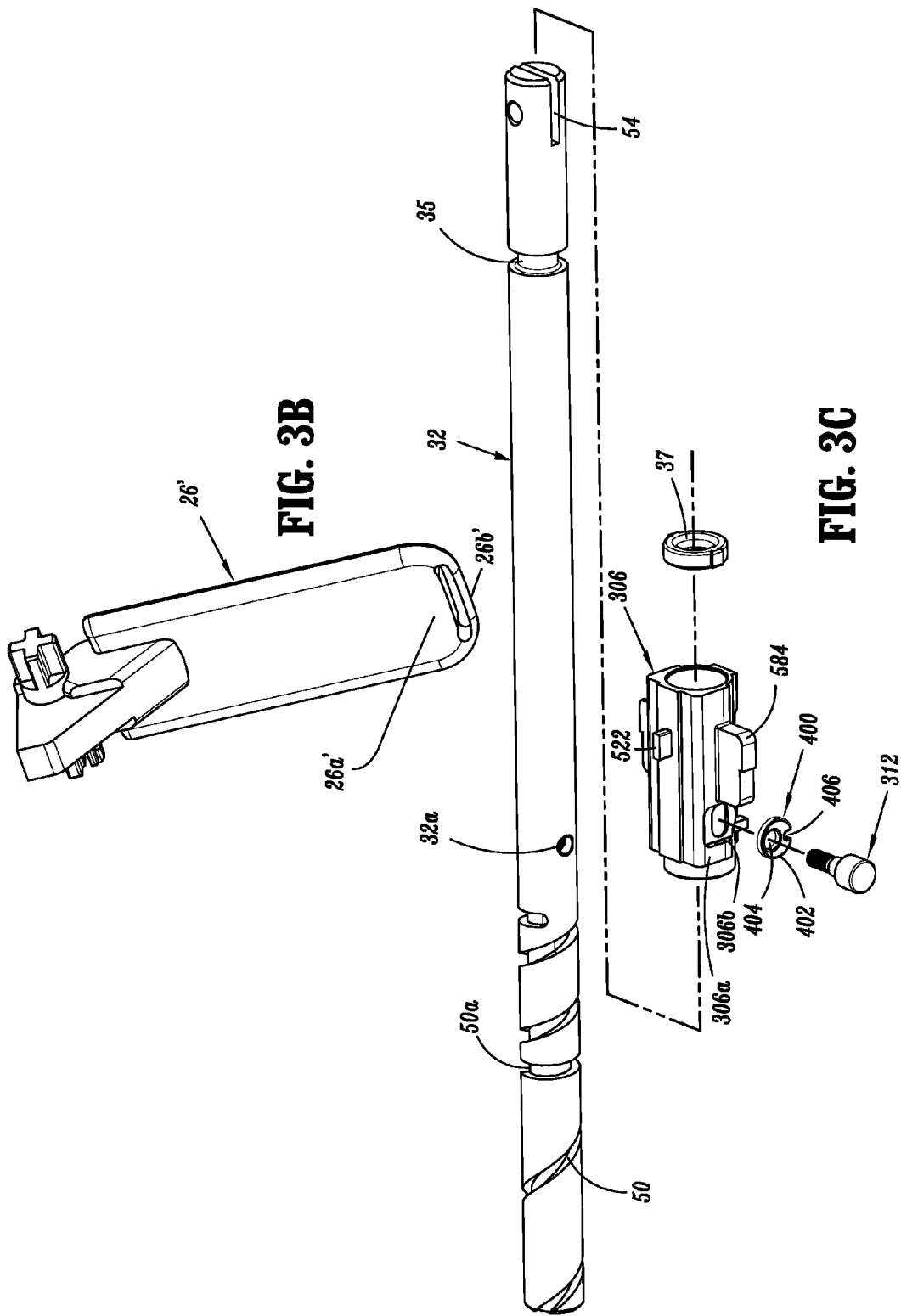

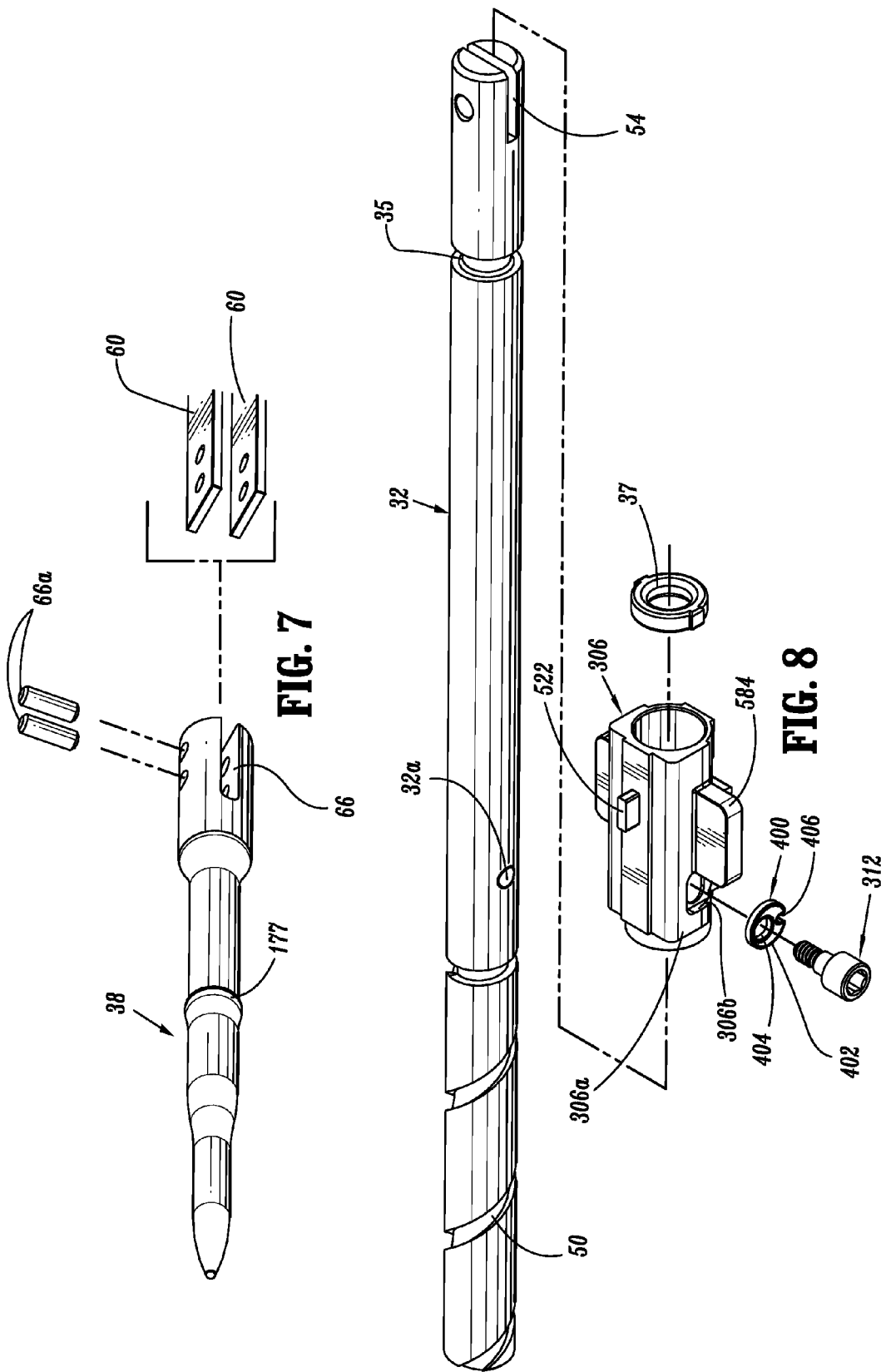

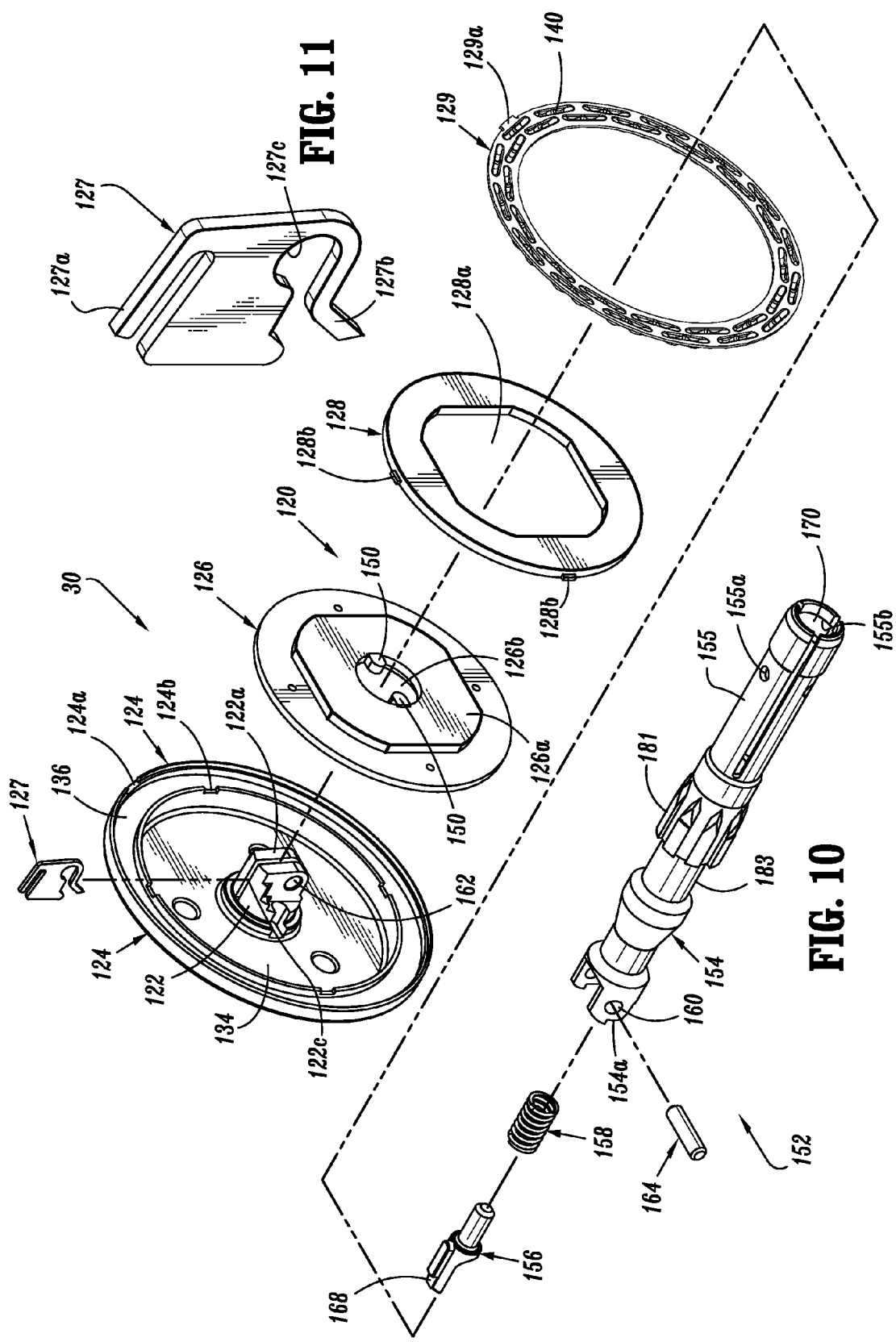

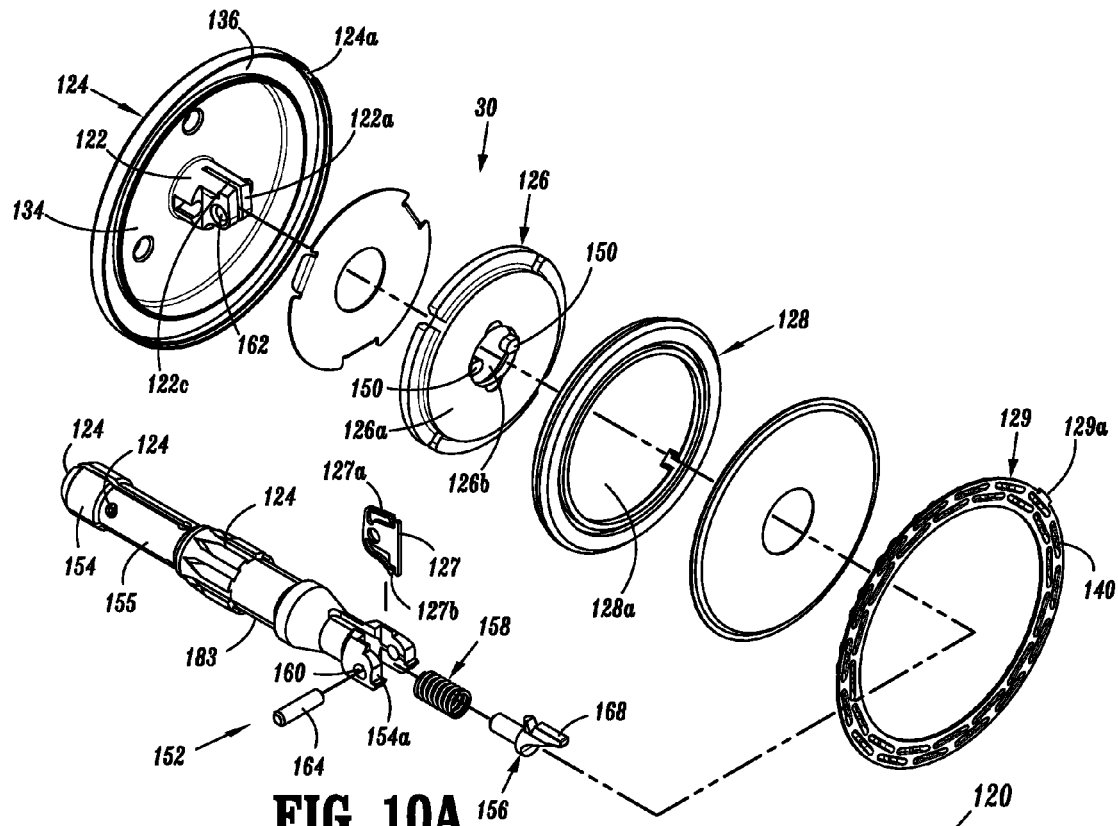
FIG. 10A
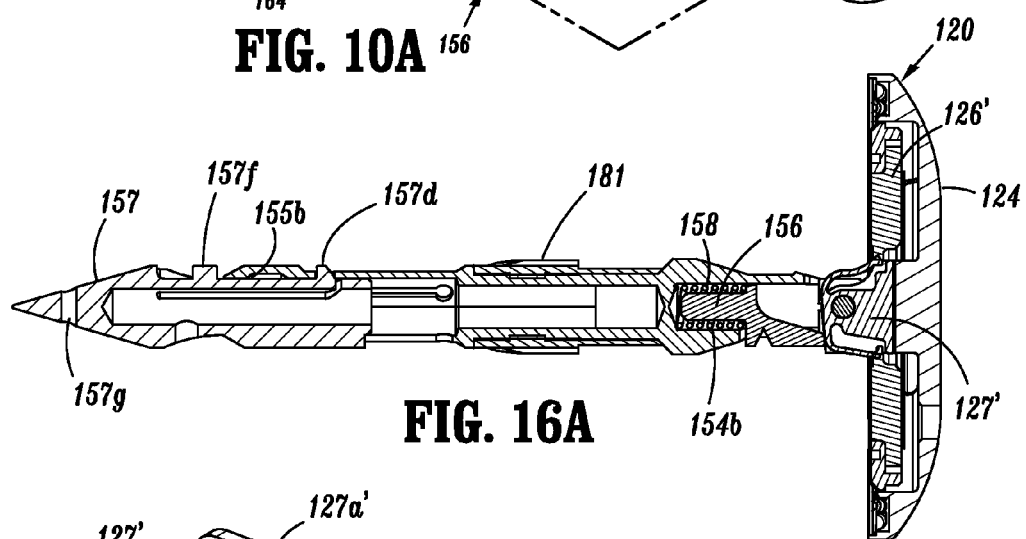
FIG. 16A
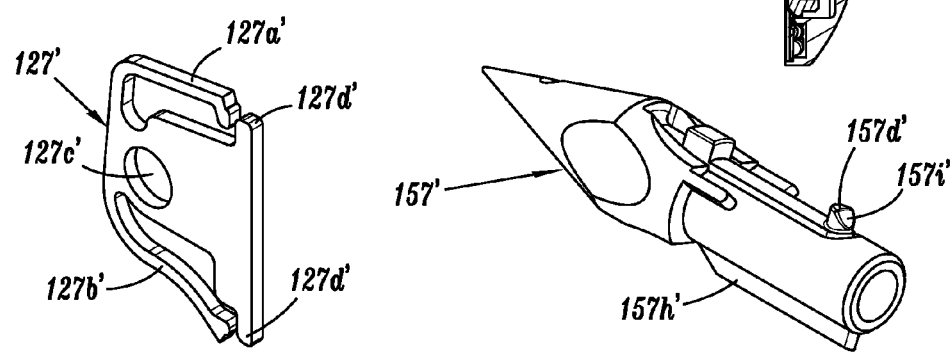
FIG. 11A   FIG. 13A

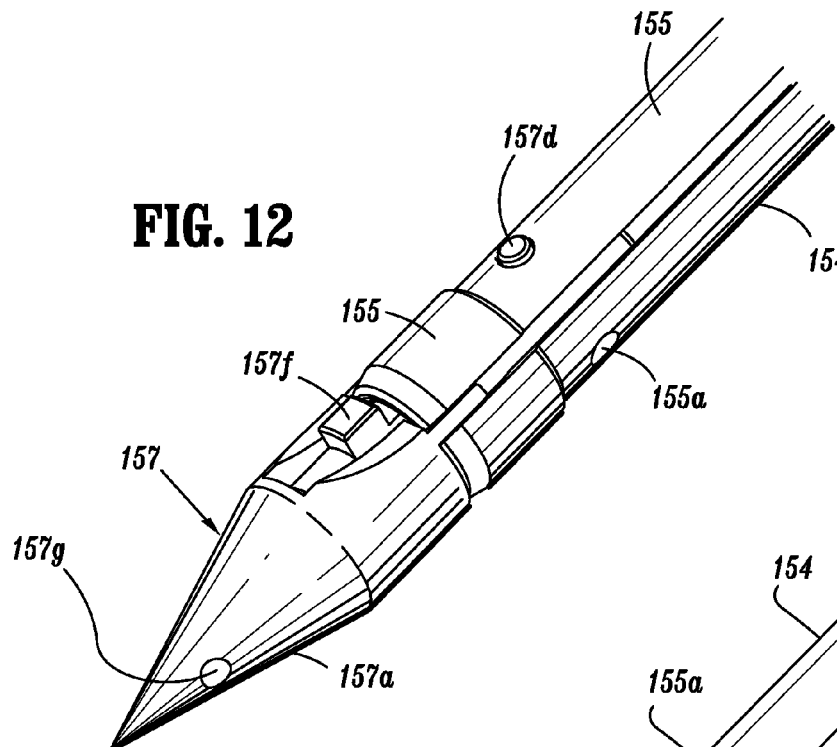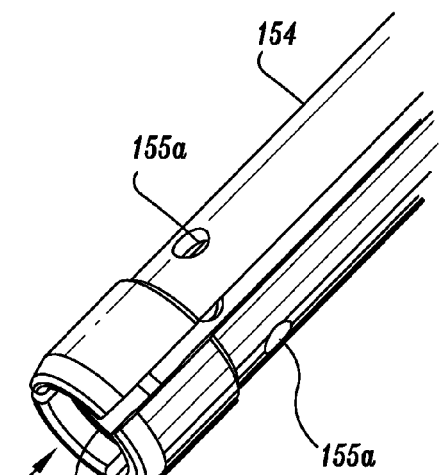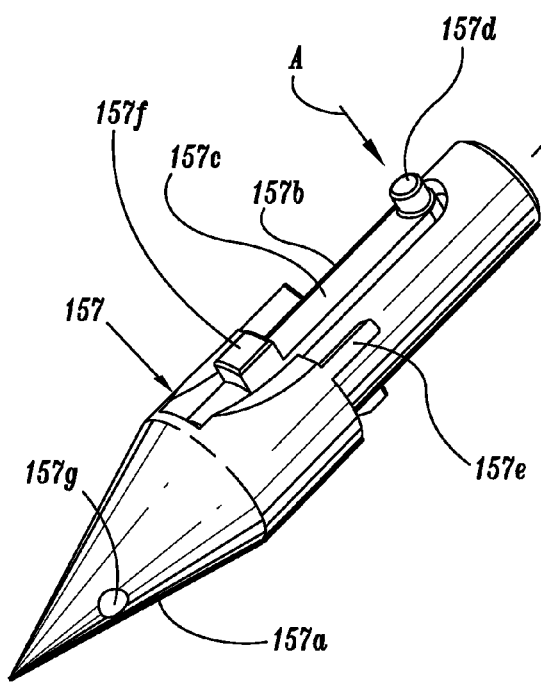

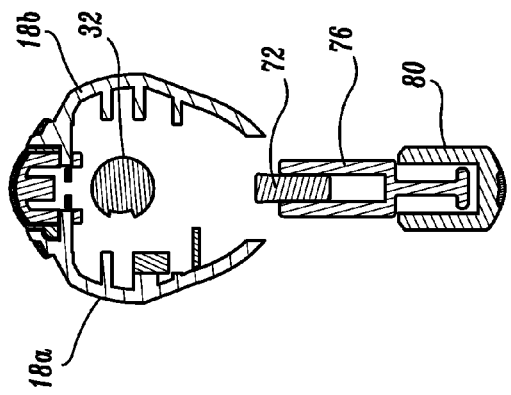
FIG. 41
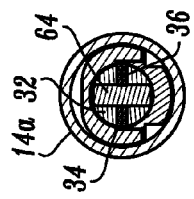
FIG. 44
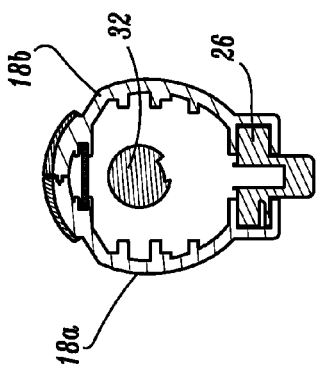
FIG. 40
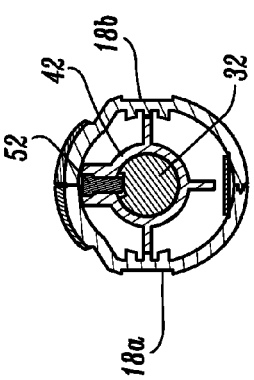
FIG. 43
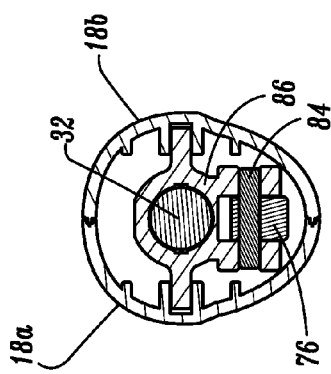
FIG. 39
FIG. 42

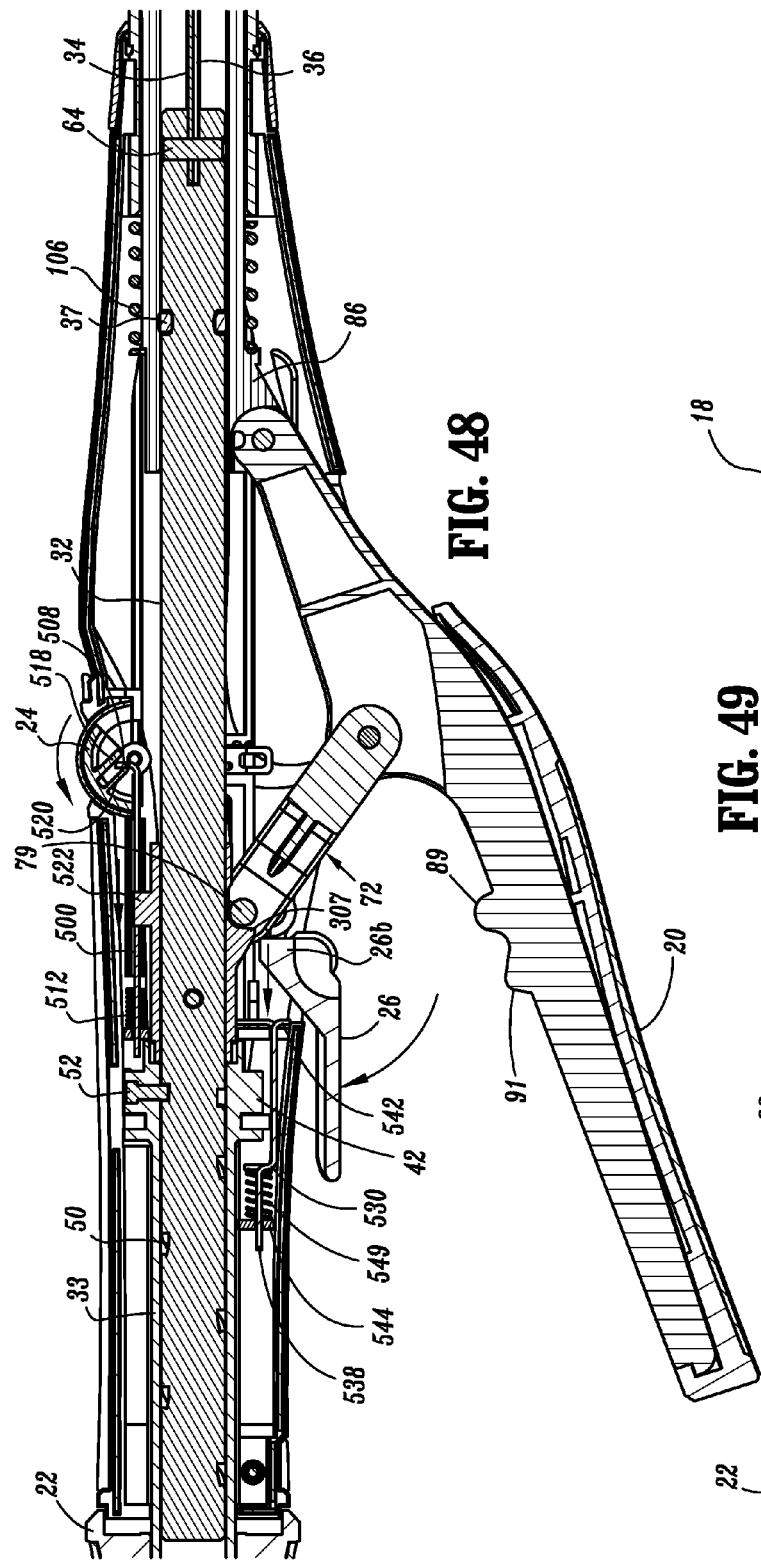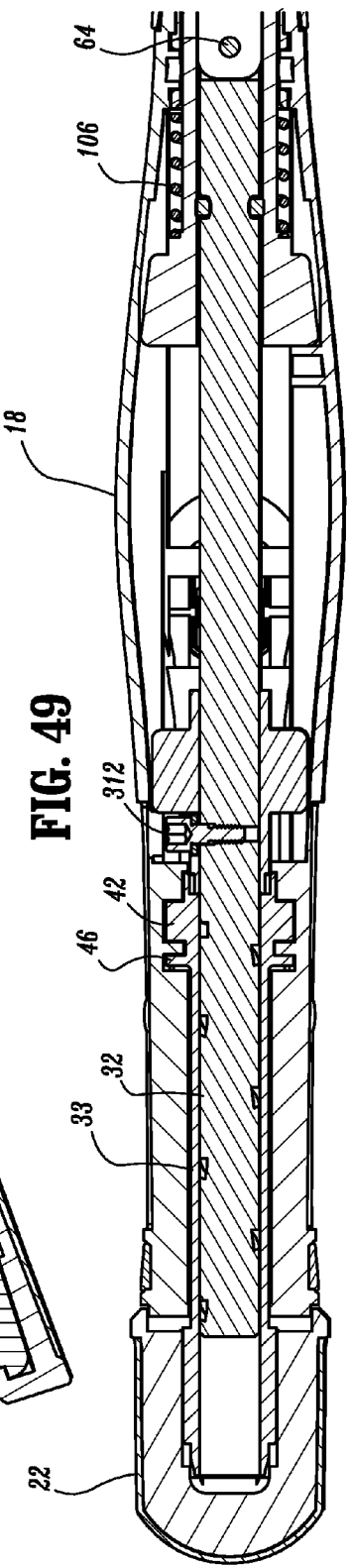

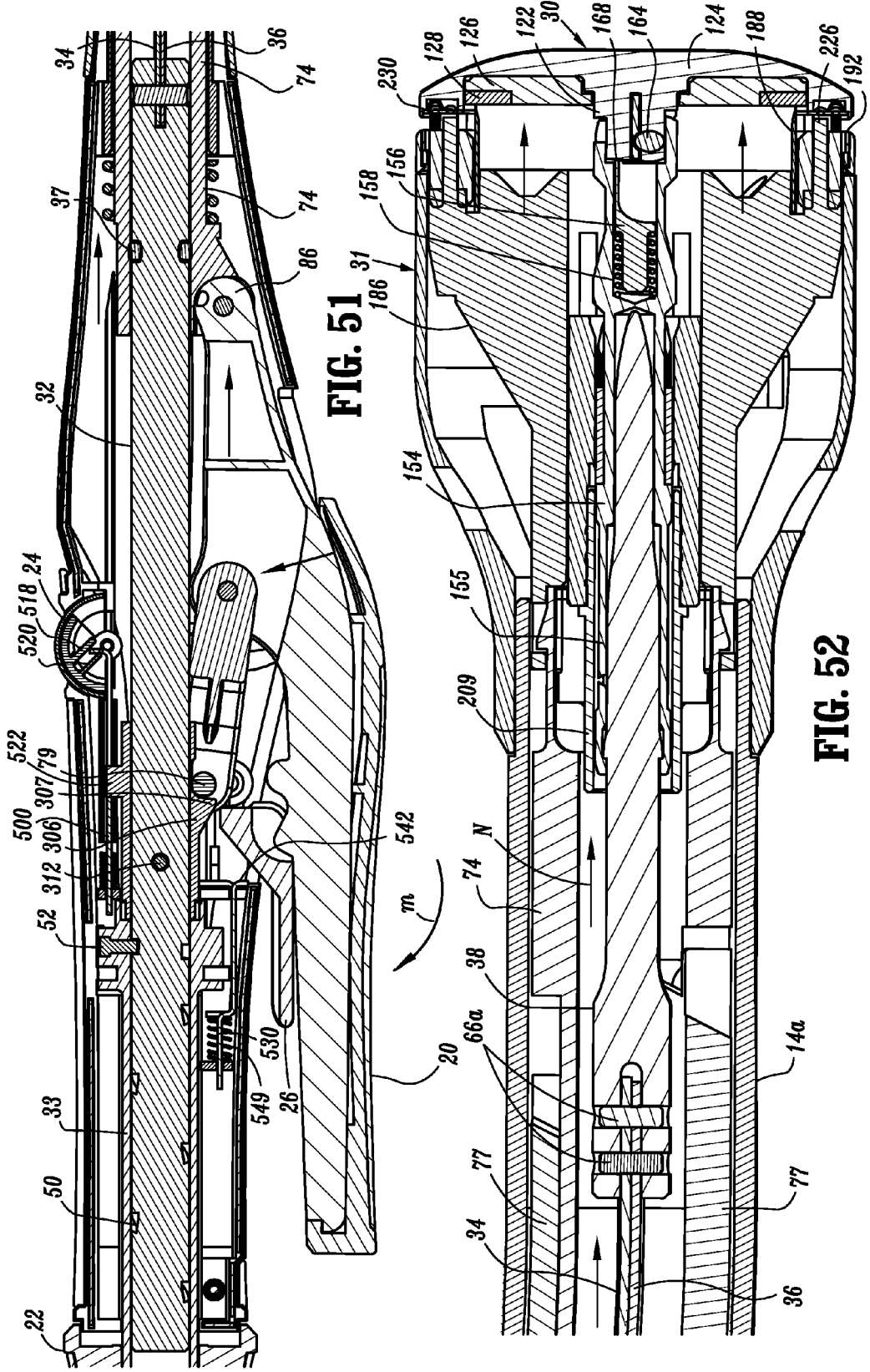

US 8,348,122 B2

SURGICAL STAPLING DEVICE

CROSS REFERENCE TO RELATED APPLICATIONS

This application is a continuation-in-part of U.S. patent application Ser. No. 10/528,975, filed Mar. 23, 2005, now U.S. Pat. No. 7,303,106, which claims the benefit of and priority to PCT Application Serial No. PCT/US03/31638, filed Oct. 6, 2003, which claims the benefit of and priority to U.S. Provisional Application Ser. No. 60/416,055, filed Oct. 4, 2002, now expired, the entire contents of all of which being incorporated by reference herein. This application also claims priority to and the benefit of U.S. Provisional Application Ser. No. 60/714,141 filed Sep. 2, 2005.

BACKGROUND

1. Technical Field

The present disclosure relates generally to a surgical stapling device for applying surgical staples to body tissue. More particularly, the present disclosure relates to a surgical stapling device suitable for performing circular anastomosis of hollow tissue organs.

2. Background to Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end adjacent the staple holding component. Opposed end portions of tissue of the organs to be stapled are clamped between the anvil head and the staple holding component. The clamped tissue is stapled by driving one or more staples from the staple holding component so that the ends of the staples pass through the tissue and are deformed by the anvil head.

In use, the staple holding component and anvil assembly are positioned within opposed sections of the organs to be joined and are not visible to the surgeon. Typically, an indicator is provided on the stapling device which is visible to the surgeon to identify when the anvil assembly and staple holding portion have been sufficiently approximated such that the device is in a fire-ready position. Conventional indicators include indicia which is moved to a position visible to a surgeon when the device has been approximated. Such indicia is sometimes difficult to view.

Accordingly, a need exists for a stapling device with an approximation/fire-ready indicator which prominently displays indicia which is easily viewable by a surgeon.

SUMMARY

In accordance with the present disclosure, a surgical stapling device is disclosed which includes a handle assembly having a stationary handle, a firing trigger and a rotatable approximation knob. An elongated body portion extends distally from the handle assembly. A head portion including an anvil assembly and a shell assembly is positioned at the distal end of the body portion. The shell assembly supports a plurality of staples. An approximation mechanism includes the approximation knob, a drive screw and an anvil retainer. The anvil retainer is operably connected to the drive screw. The drive screw includes a helical channel having a first pitch. The approximation knob is operably connected to a pin which is positioned within the helical channel such that rotation of the approximation knob effects linear movement of the drive screw and anvil retainer between a first advanced position and a second retracted position. A firing mechanism includes the firing trigger and a pusher link. The firing trigger is operably connected to the pusher link such that operation of the firing trigger ejects the plurality of staples from the shell assembly. The anvil assembly includes an anvil center rod configured to releasably engage the anvil retainer. The approximation mechanism is operable to retract engaged portions of the anvil center rod and the anvil retainer within the shell assembly to lock the anvil center rod to the anvil retainer.

In one embodiment, the helical channel of the screw includes a dwell portion having a second pitch which is smaller than the first pitch. The dwell portion is positioned along the helical channel to provide a tactile indication to a surgeon that the anvil retainer has been advanced to a third position between the first advanced position and the second retracted position. In one embodiment, the third position is the position in which the anvil assembly is no longer locked to the anvil retainer assembly.

In one embodiment, the anvil center rod includes a plurality of flexible arms which are positioned to flex over and engage an annular protrusion formed about the anvil retainer. The shell assembly can include an inner guide portion having a rigid bushing dimensioned to slidably receive the engaged portions of the anvil center rod and the anvil retainer. The rigid bushing is dimensioned to provide lateral support for the flexible arms of the anvil center rod to prevent disengagement of the anvil center rod from the anvil retainer.

In one embodiment, the dwell portion of the helical channel is dimensioned to permit between about ½ to about ¾ of a turn of the approximation knob without effecting substantially any linear movement of the screw.

In one embodiment, the surgical stapling device includes a pivotable trigger lock supported on the handle assembly. The pivotable trigger lock is movable from a first position to prevent actuation of the firing trigger to a second position to permit actuation of the firing trigger. The firing trigger can include a pivotable member. The pivotable member includes first and second spaced abutments. A tip of the pivotable trigger lock is positioned between the spaced abutments when the pivotable trigger lock is in its first position. In one embodiment, the tip of the pivotable trigger lock includes a flexible tab which is positioned to engage the pivotable member between the spaced abutments to prevent rattling of the pivotable trigger between the spaced abutments.

A removable trocar for attachment to the center rod of an anvil assembly is also disclosed. The removable trocar includes a body having a proximal end and a distal end, a trocar tip formed at the distal end of the body and a cantilevered arm extending along a longitudinal axis of the body. The cantilevered arm includes a distal end secured to the body and a proximal end having a protrusion formed thereon. In one embodiment, the protrusion is dimensioned to be releasably received within an opening of an anvil center rod. The body also includes a rib extending proximally of the protrusion. The rib is dimensioned to slide between flexible arms of an anvil center rod to properly align the projection with the opening of the anvil center rod.

The projection can include an angled proximal face. The cantilevered arm can include a distal tab which is positioned to facilitate deflection of the cantilevered arm to disengage the projection from an anvil center rod. In one embodiment, the body includes at least one spline offset from the rib. A throughbore can be provided in the body which is dimensioned to receive a suture.

BRIEF DESCRIPTION OF THE DRAWINGS

Various preferred embodiments of the presently disclosed surgical stapling device are disclosed herein with reference to the drawings wherein:

FIG. 3' is a side perspective exploded view of an alternate embodiment of the handle assembly of the presently disclosed surgical device;

FIG. 3A is a top perspective view of the indicator of the handle assembly shown in FIG. 3;

FIG. 3B is a side perspective view of an alternate embodiment of the trigger lock of the presently disclosed surgical device;

FIG. 3C is a side perspective view of an alternative embodiment of a drive screw of the presently disclosed surgical device including a dwell portion;

FIG. 7 is an enlarged side perspective of the anvil retainer and band portions of the central body portion shown in FIG. 6;

FIG. 8 is a side perspective view of the screw and screw stop of the approximation mechanism of the handle assembly shown in FIG. 5;

FIG. 10 is a side perspective exploded view from the proximal end of the anvil assembly of the surgical stapling device shown in FIG. 1;

FIG. 10A is a side perspective exploded view from the proximal end of an alternate embodiment of the anvil assembly of the surgical stapling device shown in FIG. 1;

FIG. 11 is a side perspective view of the retaining clip of the anvil assembly shown in FIG. 10;

FIG. 11A is a side perspective view of the retainer clip of the anvil assembly shown in FIG. 10A;

FIG. 12 is a side perspective view of the distal end of the center rod of the anvil assembly shown in FIG. 10 with a removable trocar fastened thereto;

FIG. 13 is a side perspective view of the center rod and removable trocar shown in FIG. 11 separated one from the other;

FIG. 13A is a side perspective view of an alternate embodiment of the trocar shown in FIG. 13;

FIG. 16A is a side cross-sectional view of the anvil assembly shown in FIG. 10A with the trocar shown in FIG. 13A supported therein;

FIG. 39 is a cross-sectional view taken along section lines 39-39 of FIG. 38;

FIG. 40 is a cross-sectional view taken along section lines 40-40 of FIG. 38;

FIG. 41 is a cross-sectional view taken along section lines 41-41 of FIG. 38;

FIG. 42 is a cross-sectional view taken along section lines 42-42 of FIG. 38;

FIG. 43 is a cross-sectional view taken along section lines 43-43 of FIG. 38;

FIG. 44 is a cross-sectional view taken along section lines 44-44 of FIG. 38;

FIG. 48 is a side cross-sectional view of the handle assembly of the surgical stapling device shown in FIG. 45;

FIG. 49 is a top horizontal cross-sectional view of a portion of the handle assembly of the surgical stapling device shown in FIG. 45;

FIG. 51 is a side cross-sectional view of a portion of the handle assembly of the surgical stapling device shown in FIG. 45 after the firing trigger has been actuated;

FIG. 52 is a side cross-sectional view of the distal end of the surgical stapling device shown in FIG. 45 after the firing trigger has been actuated;

DETAILED DESCRIPTION OF PREFERRED EMBODIMENTS

Figure 1:
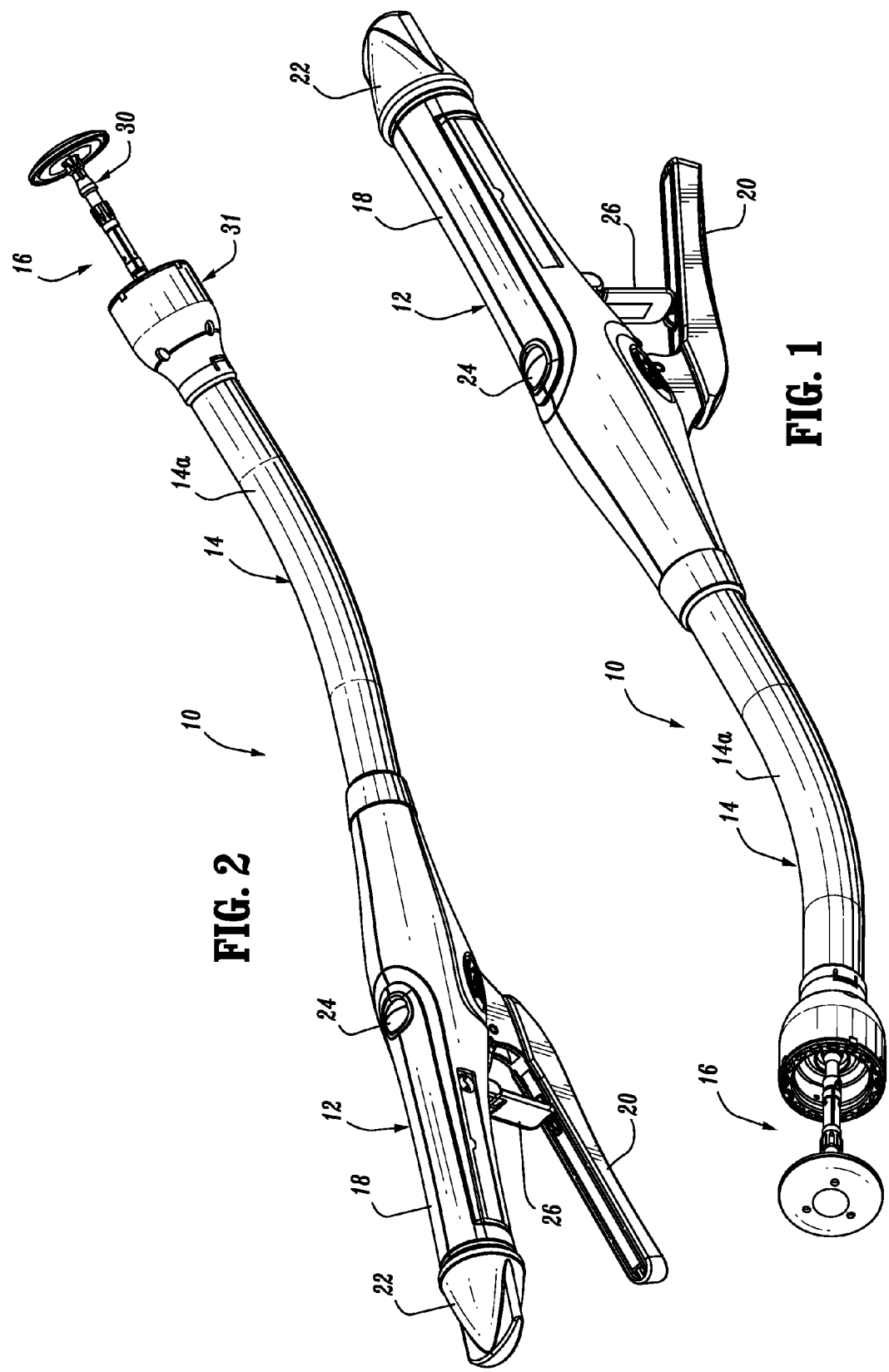
FIG. 1 is a top side perspective view from the proximal end of the presently disclosed surgical stapling device in the unapproximated position.

Preferred embodiments of the presently disclosed surgical stapling device will now be described in detail with reference to the drawings in which like reference numerals designate identical or corresponding elements in each of the several views.

Throughout this description, the term "proximal" will refer to the portion of the instrument closest to the operator and the term "distal" will refer to the portion of the instrument furthest from the operator.

Figure 2:
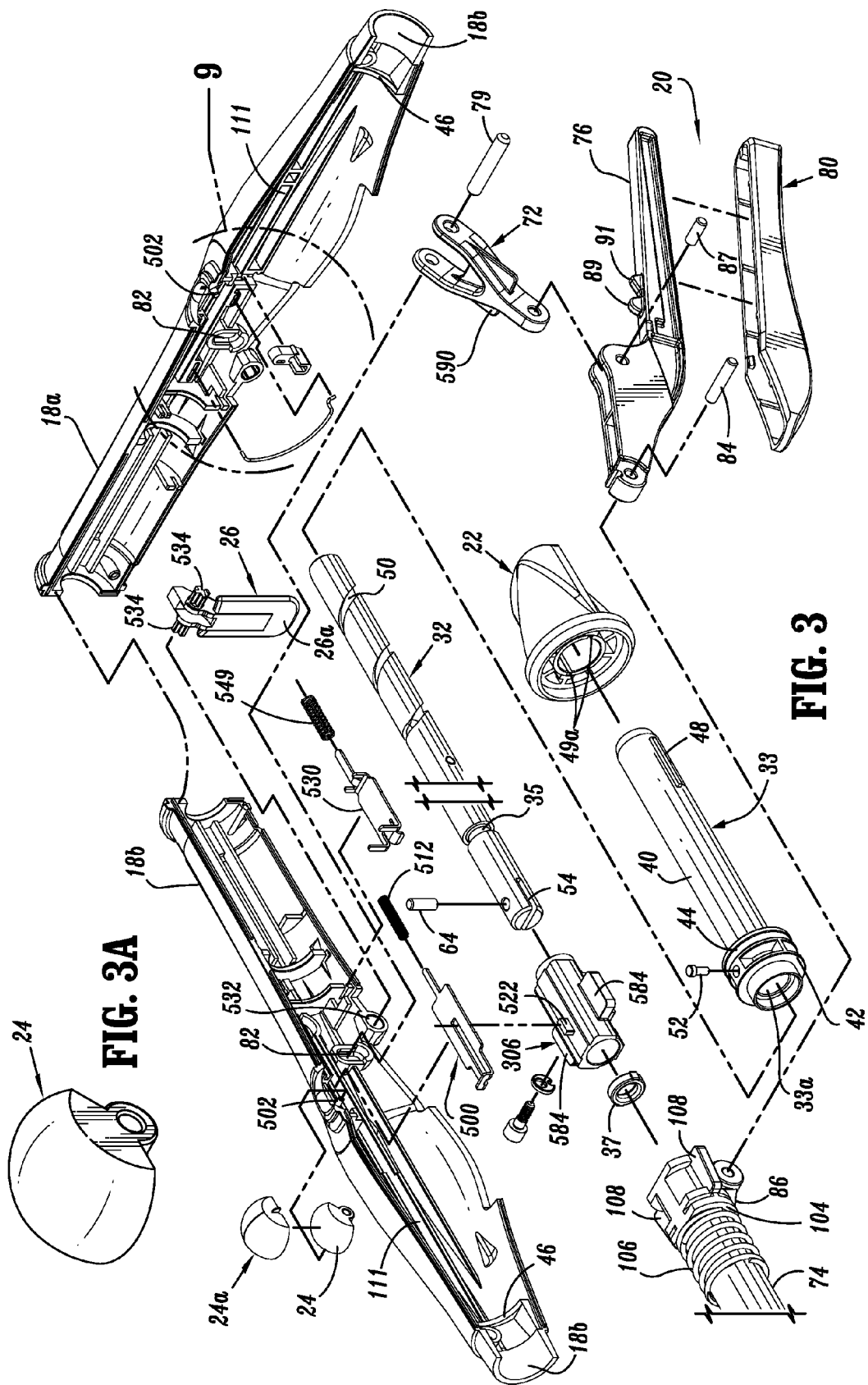
FIG. 2 is a top side perspective view from the distal end of the surgical stapling device shown in FIG. 1.

FIGS. 1 and 2 illustrate one preferred embodiment of the presently disclosed surgical stapling device shown generally as 10. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, preferably shortened, central body portion. The length, shape and/or the diameter of body portion 14 and head portion 16 may also be varied to suit a particular surgical procedure.

Handle assembly 12 includes a stationary handle 18, a firing trigger 20, a rotatable approximation knob 22 and an indicator 24. Stationary handle 18 is preferably formed from thermoplastic handle sections 18a and 18b, e.g., polycarbonate, (FIG. 3) which together define a housing for the internal components of handle assembly 12. Handle sections 18a and 18b are preferably secured together by sonic welding. Alternately, other known securement techniques may be employed including screws, adhesives, snap-fit connectors, etc. The internal components of handle portion 12 will be discussed in detail below. Preferably, cushioned and/or resilient slip resistant portions such as a grip (not shown) can be fastened to or included as part of handle sections 18a and 18b and firing trigger 20. The slip resistant grip may be formed over handle sections 18a and 18b and firing trigger 20 using an overmolding procedure and may be formed from neoprene or rubber. Alternately, other suitable materials, e.g., elastomeric materials, and joining techniques may be employed. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alphanumeric labeling, etc., to identify to a surgeon whether the device is approximated and is ready to be fired. Indicator 24 preferably has a bulbous or convex shape which extends outwardly from a top surface of handle sections 18a and 18b and is easily viewable by a surgeon from the top and sides of the stapling device.

Head portion 16 includes an anvil assembly 30 and a shell assembly 31. Each of these assemblies will be discussed in detail below. Except where otherwise noted, the components of surgical device 10 are generally formed from thermoplastics including polycarbonates, and metals including stainless steel and aluminum. The particular material selected to form a particular component will depend upon the strength requirements of the particular component. For example, the anvil is preferably formed from a metal, such as stainless steel, and the stationary handle is preferably formed from a thermoplastic such as polycarbonate. Alternately, other materials not listed above, which preferably can withstand sterilization procedures, may be used to form components of stapling device 10 provided the materials are suitable for surgical use and meet the strength requirements of the particular component.

Figure 3:
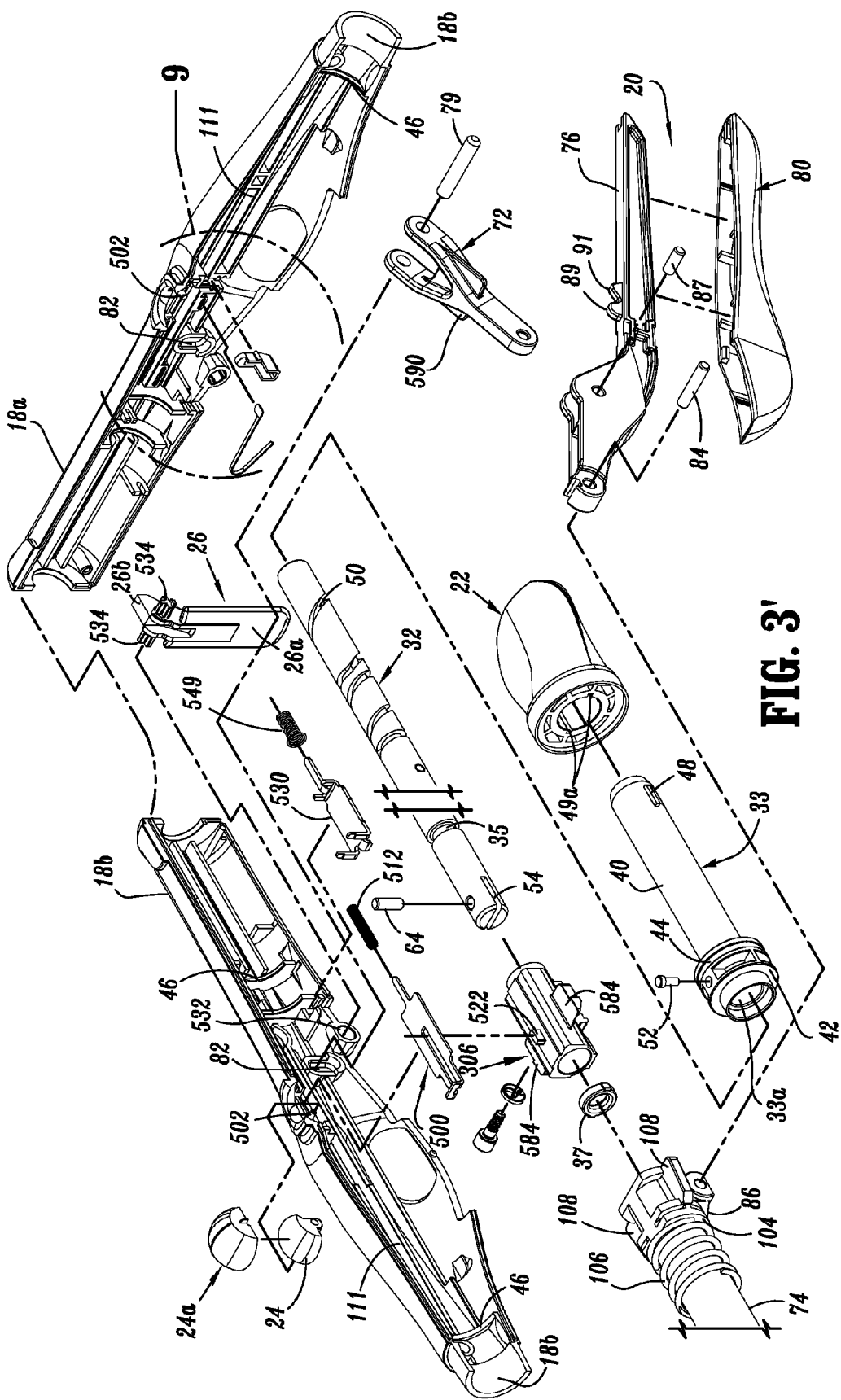
FIG. 3 is a side perspective exploded view of the handle assembly of the surgical stapling device shown in FIG. 1.
Figure 4:
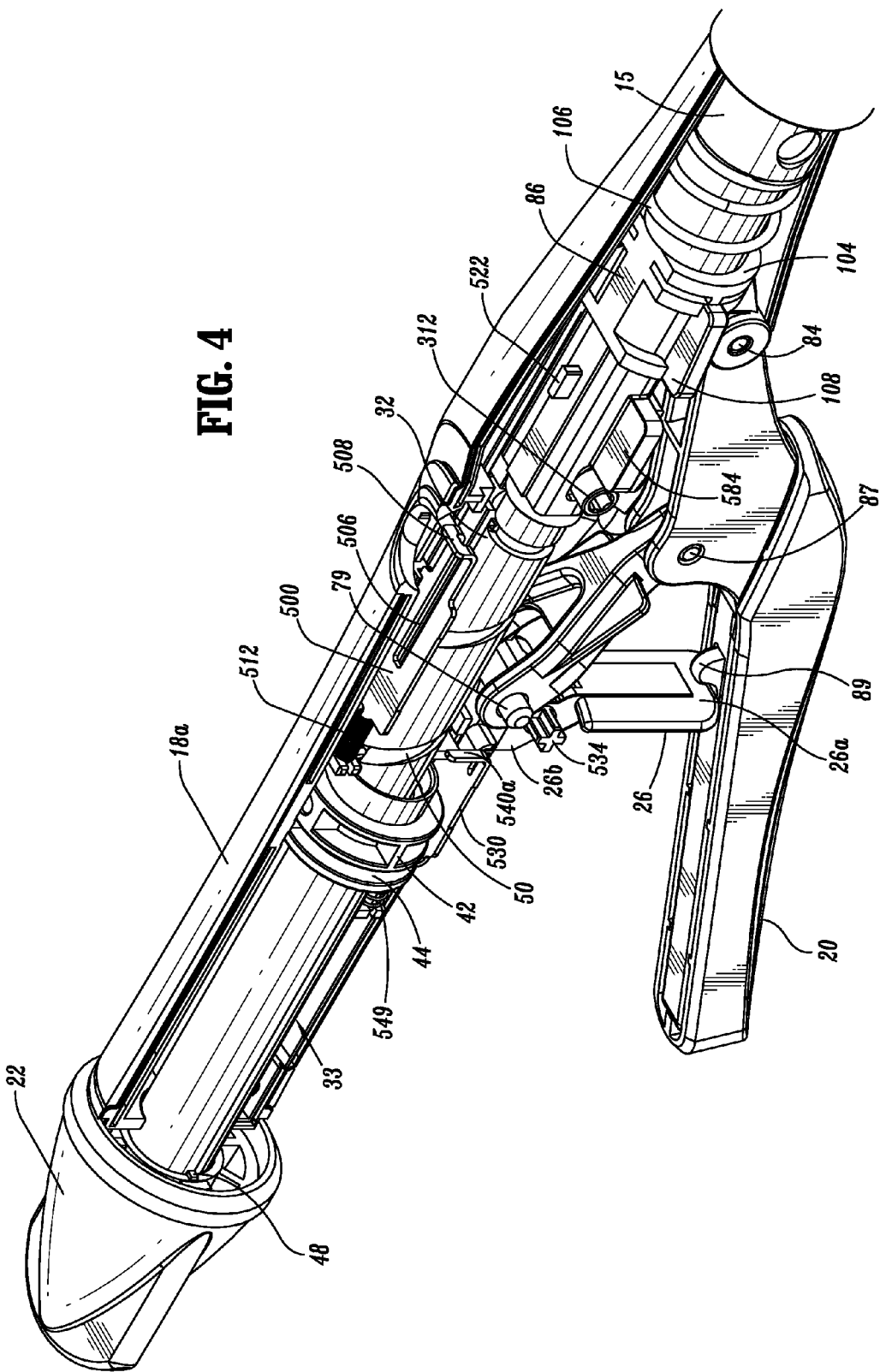
FIG. 4 is a side perspective view from the top of the handle assembly of the surgical stapling device shown in FIG. 1 with a handle section removed.
Figure 5:
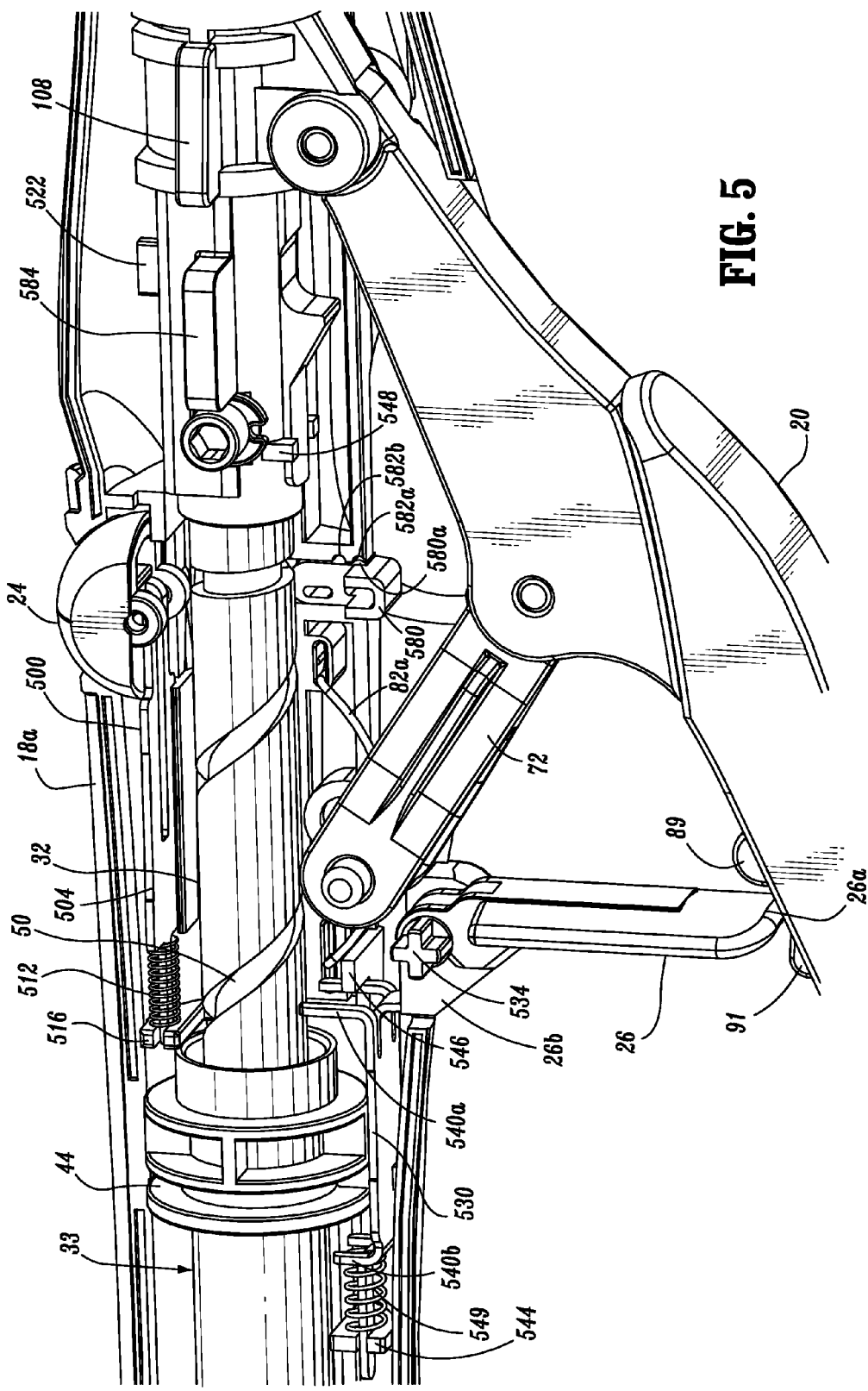
FIG. 5 is a side perspective view from the bottom of the handle assembly of the surgical stapling device shown in FIG. 4.
Figure 6:
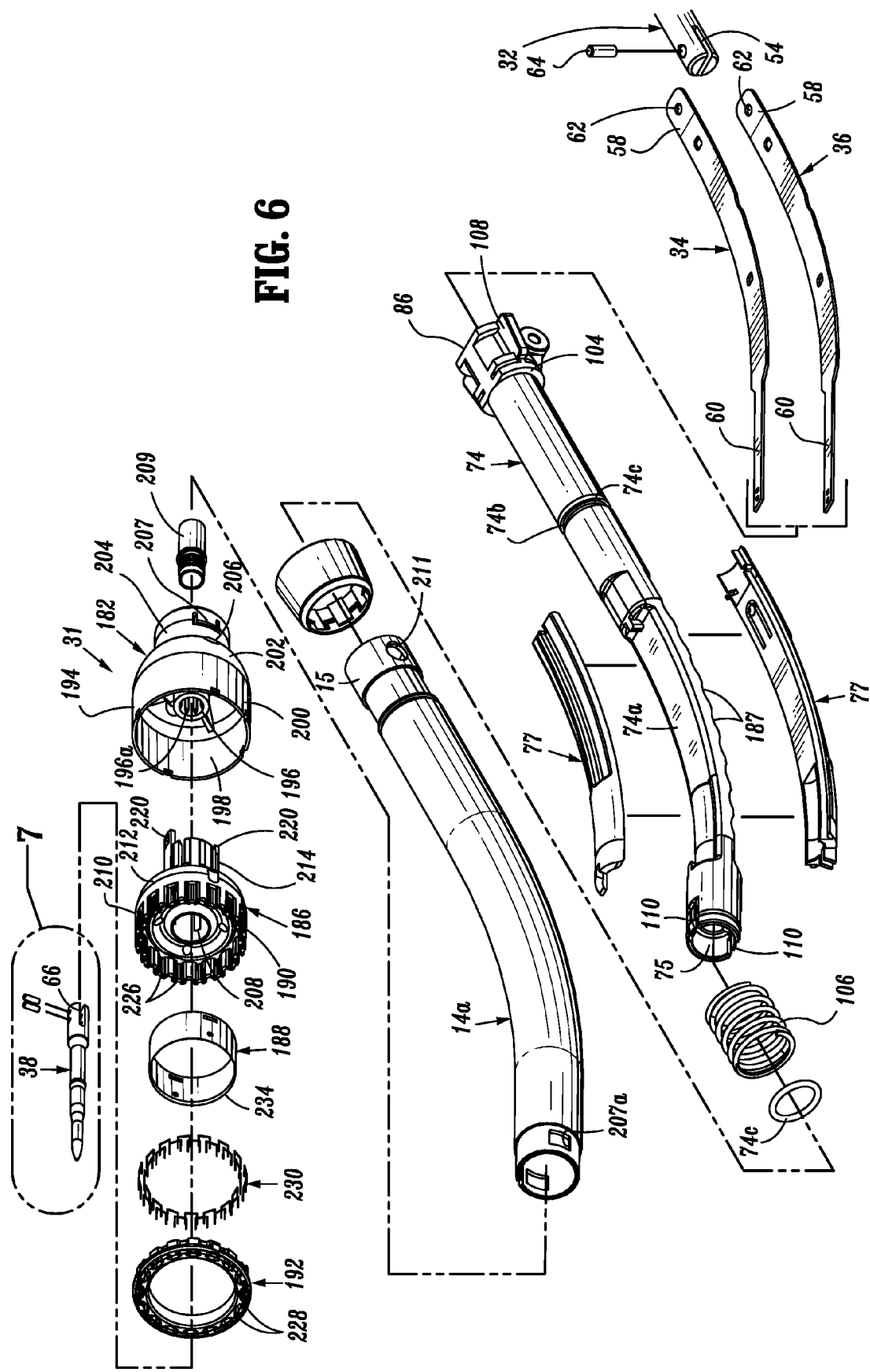
FIG. 6 is a side perspective exploded view of the central body portion and distal head portion of the surgical stapling device shown in FIG. 1.
Figure 9A:
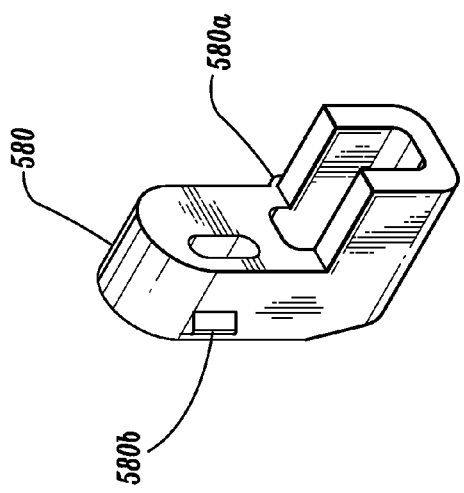
FIG. 9A is a side perspective view from the top of the abutment member of the handle assembly shown in FIG. 3.
Figure 9:
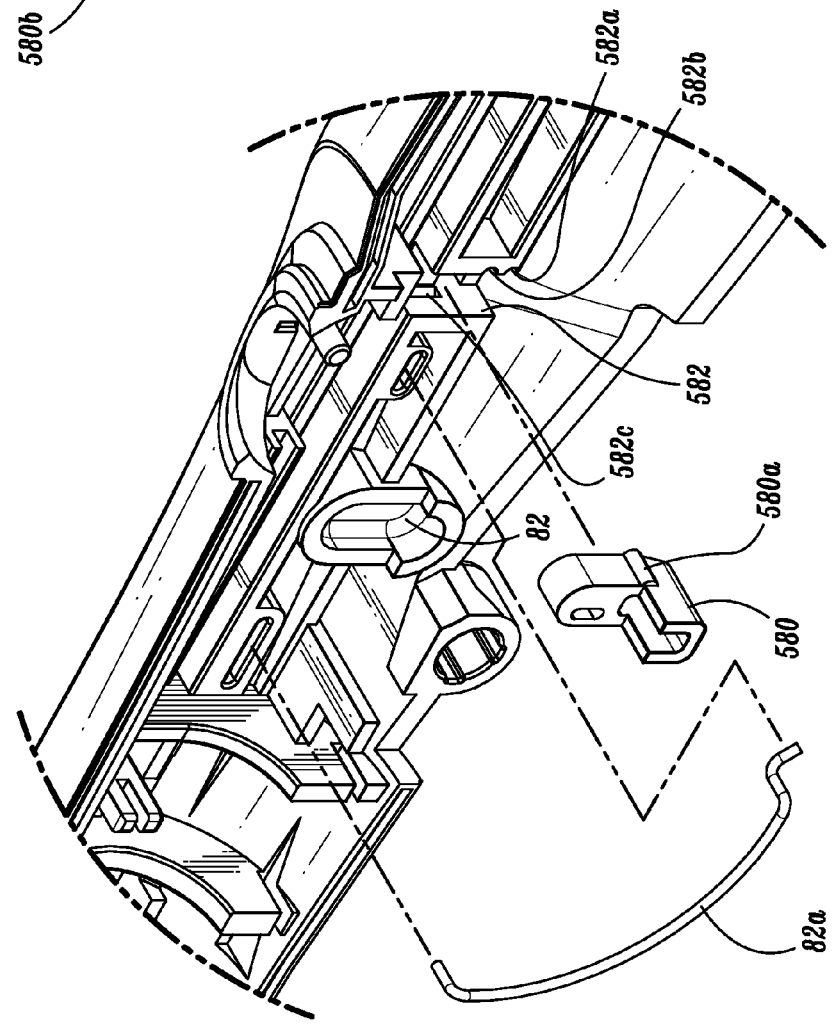
FIG. 9 is an enlarged view of the indicated area of detail shown in FIG. 3.

FIGS. 3-5 illustrate the internal components of handle assembly 12. The internal components include the proximal components of approximation and firing mechanisms, a firing lockout mechanism and an indicator drive mechanism. FIGS. 6 and 7 illustrate the internal components of elongated body portion 14. These components include the distal components of the approximation and firing mechanisms. Each of these mechanisms will be disclosed in detail hereinbelow.

Approximation Mechanism

Referring to FIGS. 3-8, the approximation mechanism includes approximation knob 22, a drive screw 32, a rotatable sleeve 33, first and second screw extensions 34 and 36 (FIG. 6), respectively, and an anvil retainer 38. Rotatable sleeve 33 includes a substantially cylindrical hollow body portion 40 and a substantially cylindrical collar 42 which together define a central bore 33a. Collar 42 has an annular groove 44 formed thereabout which is dimensioned to receive an inwardly extending flange 46 formed on an inner wall of handle sections 18a and 18b. Engagement between groove 44 and flanges 46 axially fixes sleeve 33 within handle 18 while permitting rotation of sleeve 33 in relation to stationary handle 18. The proximal end of body portion 40 of rotatable sleeve 33 extends through an opening 18b in the proximal end of stationary handle 18. A pair of diametrically opposed elongated ribs 48 are positioned or formed on the outer surface of body portion 40. Approximation knob 22 includes a pair of internal slots 49a positioned to receive ribs 48 of sleeve 33 to rotatably fix sleeve 33 to knob 22, such that rotation of knob 22 causes concurrent rotation of sleeve 33.

The proximal half of screw 32 includes a helical channel 50 and is dimensioned to be slidably positioned within central bore 33a of rotatable sleeve 33. The distal end of screw 32 includes an annular recess 35 dimensioned to receive a seal member 37 (FIG. 3) for providing a fluid tight seal between the outer surface of screw 32 and the inner surface of pusher link 74. A pin 52 (FIG. 3) extends radially through cylindrical collar 42 of sleeve 33 into helical channel 50. Since sleeve 33 is axially fixed with respect to stationary handle 18, rotation of sleeve 33 about screw 32 causes pin 52 to move along channel 50 of screw 32 to effect axial movement of screw 32 within stationary handle 18. In an alternate embodiment, helical channel 50 includes a dwell portion 50a (FIGS. 3' and 3C). When pin 52 is positioned in dwell portion 50a, the pitch of channel 50 is such that rotation of sleeve 33 effects substantially no axial movement of screw 32. As illustrated in FIG. 3C, the helical channel 50 defines a first pitch which is greatest at the proximal end of helical channel 50, a second lesser pitch at a distal end of helical channel 50 and a third pitch which is less than the second pitch at dwell portion 50a of helical channel 50. The third pitch is positioned between the first and second pitches of the helical channel.

Referring to FIGS. 6-8, the distal end of screw 32 includes a transverse slot 54. Top and bottom screw extensions 34 and 36 (FIG. 6) each include a proximally located flexible flat band portion 58 and a distally located flat band portion 60. Alternately, it is envisioned that screw extensions 34 and 36 may have other than a band configuration. For example, screw extensions 34 and 36 may be semi-circular or circular in cross-section. The flexibility of top and bottom screw extensions 34 and 36 permits movement of screw extensions 34 and 36 through curved elongated body portion 14. The proximal end of each band portion 58 includes a hole 62 dimensioned to receive a pin 64 for securing the proximal end of screw extensions 34 and 36 within transverse slot 54 of screw 32. Alternately, other fastening techniques may be used to secure each band portion 58 to screw 32, e.g., welding, crimping, etc. Distally located band portion 60 of each screw extension 34 and 36 is dimensioned to be received within a transverse slot 66 formed in a proximal end of anvil retainer 38 (FIG. 7) to fasten anvil retainer 38 to the distal end of screw extensions 34 and 36. Preferably, a pair of pins 66a which extend through the proximal end of anvil retainer 38 and band portions 60 are used to secure screw extensions 34 and 36 to anvil retainer 38. Alternately, band portions 60 can be brazed or welded within slot 66 or other fastening techniques may be used to secure band portions 60 of screw extensions 34 and 36 to anvil retainer 38, e.g., screws, crimping, etc. Anvil retainer 38 includes an annular protrusion 177 (FIG. 7) which is configured to engage the anvil assembly in a manner to be discussed in detail below. Alternately, protrusion 177 need not be annular or may include different attachment structure, e.g., recesses, grooves, etc.

Referring again to FIGS. 3-7, when approximation knob 22 is manually rotated, rotatable sleeve 33 is rotated about the proximal end of screw 32 to move pin 52 along helical channel 50 of screw 32. Since sleeve 33 is axially fixed to stationary handle 18, as pin 52 is moved through channel 50, screw 32 is advanced or retracted within stationary handle 18 except when pin 52 is positioned within dwell 50a. As a result, top and bottom screw extensions 34 and 36, which are fastened to the distal end of screw 32, and anvil retainer 38, which is fastened to the distal end of screw extensions 34 and 36, are moved axially within elongated body portion 14. Since anvil assembly 30 is secured to the distal end of anvil retainer 38, rotation of approximation knob 22 will effect movement of anvil assembly 30 in relation to shell assembly 31 between spaced and approximated positions. Dwell 50a in channel 50 permits about ½ to ¾ of a turn of approximation knob 22 without any substantial axial movement of screw 32 to identify to a surgeon that anvil assembly 30 has been unapproximated a distance sufficient to allow tilting of anvil head assembly 120 as will be discussed below. Dwell 50a may also be positioned on screw 32 to provide an indicator to a surgeon that anvil assembly 30 has been unapproximated a distance sufficient to allow removal of anvil assembly 30 from anvil retainer 38 as will be discussed in further detail below.

Firing Mechanism

Referring to FIGS. 3-6 and 9, the firing mechanism includes firing trigger 20, a firing link 72 and an elongated pusher link 74 (FIG. 6). Firing trigger 20 includes a body portion 76 and a trigger cover 80. A cushioned gripping surface (not shown) preferably formed of neoprene or rubber is provided on trigger cover 80. The cushioned gripping surface provides a non-slip cushioned surface to make actuation of device 10 more comfortable to a surgeon. The distal end of body portion 76 of trigger 20 is pivotally connected to a coupling member 86 by a pivot member 84. Coupling member 86 is secured to the proximal end of pusher link 74 and may be formed integrally with pusher link 74 or as a separate element fastened thereto. Firing link 72 has a distal end pivotally secured to body portion 76 of trigger 20 by a pivot member 87 and a second end pivotally secured within a vertical slot 82 formed between stationary handle half-sections 18a and 18b of stationary handle 18 by pivot member 79.

Pivot member 79 is free to move vertically within slot 82. A spring 82a (FIG. 9) is supported within handle 18 to urge pivot member 79 downwardly towards the bottom of slot 82. Body portion 76 of trigger 20 further includes a pair of abutments including an abutment 89 and an abutment 91 which are positioned to engage the distal end 26a (FIG. 4) of trigger lock 26 in a manner to be described in greater detail below to prevent actuation of trigger 20 prior to approximation of device 10.

Coupling member 86 which is supported on the proximal end of elongated pusher link 74 includes a flange 104 (FIG. 6). A spring 106 is positioned between a proximal end 15 of outer tube 14a and flange 104 (FIG. 4) to bias pusher link 74 proximally to a retracted, non-fired position. A pair of wings 108 extend radially outwardly from coupling member 86. Wings 108 are dimensioned to slide along channels 111 (FIG. 3) formed along the internal walls of stationary handle 18 to maintain proper alignment of pusher link 74 within stationary handle 18 during firing of device 10.

Referring to FIG. 6, the distal end of pusher link 74 includes a pair of engagement fingers 110 which are dimensioned to lockingly engage with members 220 formed in the proximal end of pusher back 186. Pusher back 186 forms part of shell assembly 31 and will be discussed in greater detail below. Pusher link 74 is preferably formed from a flexible plastic material and includes a plurality of notches 187 which allow the pusher link to bend more easily as it moves through body 14. Pusher link 74 defines a hollow channel 75 for slidably receiving the approximation mechanism. A flat surface or cutout 74a (FIG. 6) formed in pusher link 74 slidably supports screw extensions 34 and 36 which are positioned in juxtaposed alignment. Spacers 77 are positioned within outer tube 14a adjacent cutout 74a to provide additional support for screw extensions 34 and 36 and pusher link 74 to prevent each component from buckling during actuation. An annular channel 74b is formed about pusher link 74 to receive an O-ring seal 74c. Pusher link 74 is slidably positioned within body portion 14 such that O-ring 74c seals the space between pusher link 74 and an internal wall of outer tube 14a. Operation of the firing mechanism of the device will be described in detail below.

Referring again to FIGS. 3-6 and 9, when firing trigger 20 is actuated, i.e., pivoted about pivot member 84, firing link 72 is moved proximally until pivot member 79 engages an abutment surface 307 (FIG. 25A-D) formed on screw stop 306 (FIG. 3). Screw stop 306 is axially fixed to screw 32 in a manner to be described in detail below. Thereafter, firing trigger 20 is pushed distally to advance pusher link 74 distally against the bias of spring 106. Since the distal end of pusher link 74 is connected to pusher back 186, actuation of firing trigger 20 effects advancement of pusher back 186 within shell assembly 31 to eject staples from shell assembly 31 in a manner to be described below.

Anvil Assembly

Referring to FIGS. 10-21, anvil assembly 30 includes an anvil head assembly 120 and an anvil center rod assembly 152. Anvil head assembly 120 includes a post 122, an anvil head 124, a backup plate 126, a cutting ring 128, a retaining clip 127 and an anvil 129. Post 122 is centrally positioned through a bore in anvil head 124. Alternately, post 122 may be integrally formed with anvil head 124. Anvil 129 is supported on anvil head 124 in an outer annular recess 136 and includes a plurality of pockets 140 for receiving and deforming staples. At least one tab 129a extends radially outwardly from anvil 129 and is dimensioned to be received within a cutout 124a formed in anvil head 124. Tab 129a and cutout 124a function to align anvil 129 within annular recess 136. Backup plate 126 includes a central opening 126b which is positioned about post 122 within an inner recess 134 of anvil head 124 between post 122 and annular recess 136. Backup plate 126 includes a raised platform 126a. Cutting ring 128 includes an opening 128a having a configuration substantially the same as platform 126a. Opening 128a is positioned about platform 126a to rotatably fix cutting ring 128a on backup ring 126. Preferably, cutting ring 128 is formed from polyethylene and is fixedly secured to backup plate 126 using, for example, an adhesive. Backup ring 126 is preferably formed from metal and provides support to cutting ring 128 to enhance the cutting of tissue. Alternately other materials of construction may be used to construct plate 126 and ring 128. Cutting ring 128 and backup plate 126 are slidably mounted about post 122. Backup plate 126 includes a pair of inwardly extending tabs 150 which will be described in further detail below. Cutting ring 128 includes tabs 128b which are received within-cutouts 124b formed in anvil head 124 to properly align backup ring 126 and cutting ring 128 within anvil head 124.

Anvil center rod assembly 152 includes anvil center rod 154, a plunger 156 and plunger spring 158. A first end of center rod 154 includes a transverse throughbore 160 which is offset from the central longitudinal axis of center rod 154. Post 122 of anvil head assembly 120 also includes a transverse throughbore 162. A pivot member 164 pivotably secures post 122 to center rod 154 such that anvil head assembly 120 is pivotably mounted to anvil center rod assembly 152. Plunger 156 is slidably positioned in a bore 154b (FIG. 16) formed in the first end of center rod 154. Plunger 156 includes an engagement finger 168 which is offset from the pivot axis of anvil head assembly 120 and biased into engagement with the base 122a of post 122 by plunger spring 158 to urge anvil head assembly 120 to a pivoted position at an angle to center rod 154. In a prefired untilted position, tabs 150 formed on backup plate 126 engage a top surface 154a (FIG. 20) of center rod 154 to prevent anvil head assembly 120 from pivoting about pivot member 164. As device 10 is fired, backup plate 126 and cutting ring 128 are moved deeper into anvil recess 134 of anvil head 124 about post 122 (FIG. 21) by knife 188 (FIG. 6) in a manner to be described in further detail below to move tabs 150 out of engagement with top surface 154a of center rod 154 to permit plunger 156 to pivot anvil head assembly 120 about pivot member 164.

Figure 17:
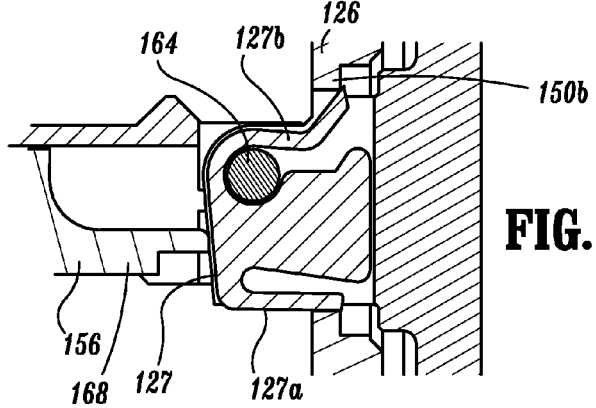
FIG. 17 is an enlarged view of the indicated area of detail shown in FIG. 16.
Figure 18:
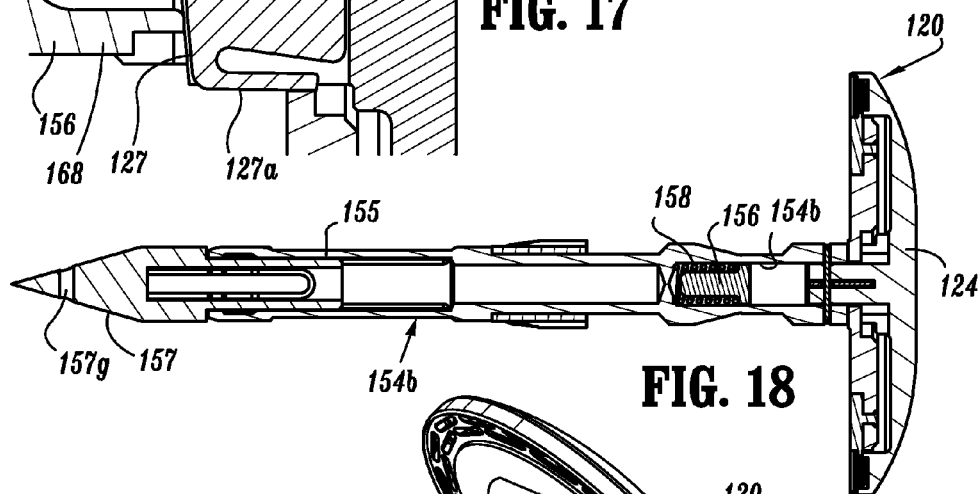
FIG. 18 is a side cross-sectional view taken through the pivot member of the anvil head assembly of the anvil assembly shown in FIG. 15.
Figure 19:
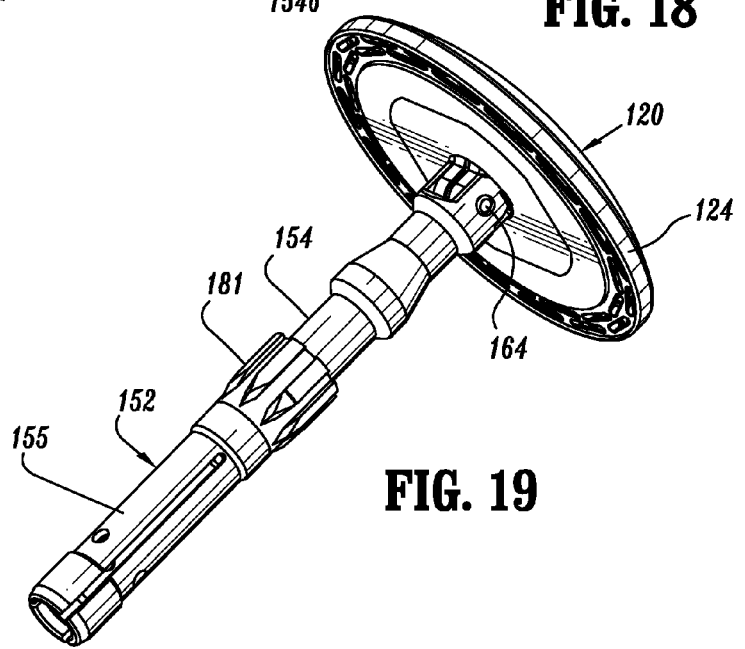
FIG. 19 is a side perspective view from the proximal end of the anvil assembly shown in FIG. 18 with the removable trocar removed.
Figure 21:
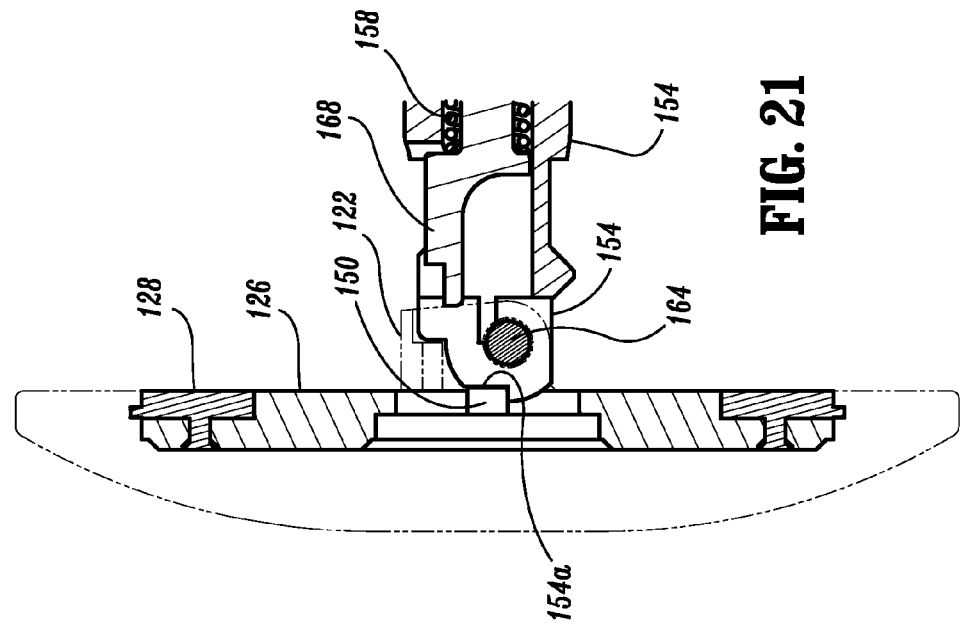
FIG. 21 is a side cross-sectional partial cutaway view of the distal portion of the anvil assembly shown in FIG. 19, with the anvil head in phantom.
Figure 20:
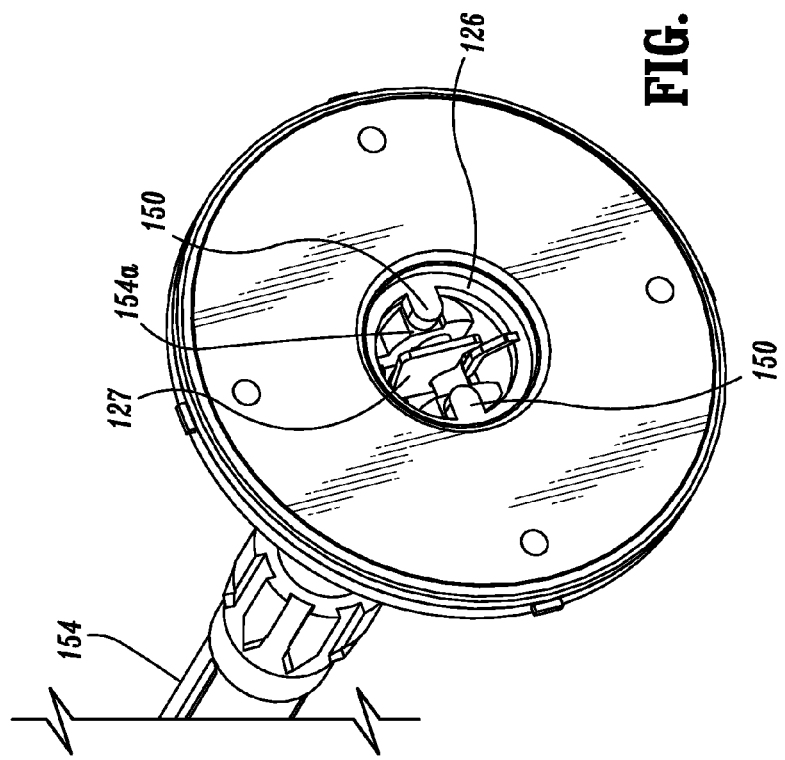
FIG. 20 is a perspective, partial cutaway view from the distal end of the anvil assembly shown in FIG. 19, with the anvil head removed.
Figure 22:
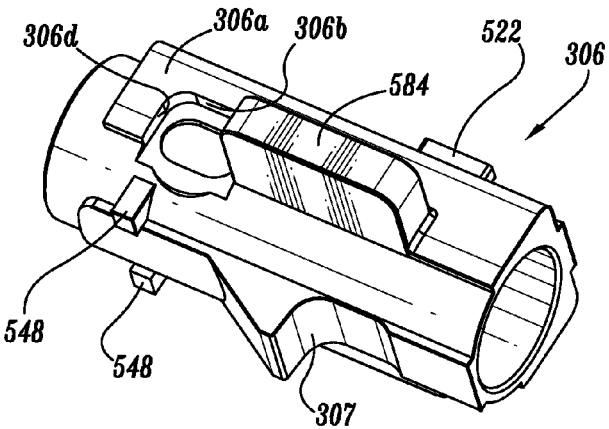
FIG. 22 is a side perspective view from the bottom of the screw stop of the handle assembly shown in FIG. 3.

A retainer clip 127 is positioned in a transverse slot 122c formed in post 122 and includes a pair of outwardly biased flexible arms 127a and 127b. Arm 127b includes a recess 127c dimensioned to receive pivot pin 164 (FIG. 17). Prior to firing device 10, arms 127a and 127b are deformed inwardly by backup plate 126 (FIG. 17). After device 10 has been fired and backup plate 126 has been pushed deeper into anvil head 124 by knife 188, flexible arms 127a and 127b spring outwardly to a position in front of backup plate 126. In this position, arms 127a and 127b prevent cutting ring 128 and backup plate 126 from sticking to the knife when anvil assembly 30 is unapproximated. It is envisioned that a retainer clip may be used in conjunction with non-pivotal anvil assemblies wherein the anvil head post and the anvil center rod are integrally formed.

FIG. 11A illustrates an alternate embodiment of the retainer clip shown generally as 127'. Retainer clip 127' also includes a pair of outwardly-biased flexible arms 127a' and 127b'. A circular bore 127c' is provided to pivotably position clip 127' about pivot pin 164 (FIG. 17). Retainer clip 127' differs from clip 127 in that clip 127' includes a pair of tabs 127d' which are positioned to engage an inner surface of backup plate 126' to prevent clip 127' from rotating out of position to engage backup plate 126' (See FIG. 16A).

A second end of center rod 154 includes a bore 170 defined by a plurality of flexible arms 155*a*. Bore 170 is dimensioned to receive a removable trocar 157. At least one of flexible arms 155, and preferably a plurality of flexible arms 155, e.g., three, include an opening 155*a* dimensioned to receive a projection 157*d* formed on removable trocar 157 to releasably secure trocar 157 to center rod 154 (FIG. 13). The distal ends of each of flexible arms 155 include an internal shoulder 155*b* (FIG. 10) dimensioned to releasably engage annular protrusion 177 of anvil retainer 38. A plurality of splines 181 are formed about center rod 154 and are dimensioned to be received within grooves 196*a* (FIG. 6) in shell assembly 31 to align anvil assembly 30 within shell assembly 31 during approximation of the anvil and shell assemblies. Center rod 154 also includes an annular recessed portion 183 to facilitate grasping of anvil assembly 30 by a surgeon with a grasper.

Referring to FIGS. 12 and 13, removable trocar 157 includes a trocar tip 157*a*, a body portion 157*b* and a cantilevered arm 157*c*. A projection 157*d* is positioned on the free end of cantilevered arm 157*c*. Arm 157*c* is deflectable downwardly, i.e., radially inwardly, in the direction indicated by arrow "A" in FIG. 13 to facilitate insertion of body portion 157*b* into bore 170 of center rod 154. Splines 157*e* or the like, preferably, are provided on body portion 157*b* to properly align trocar 157 within bore 170. Arm 157*c* biases projection 157*d* outwardly such that when projection 157*d* passes beneath opening 155*a* in center rod 154, projection 157*d* snaps outwardly into opening 155*a* to releasably secure removable trocar 157 to center rod 154. A tab 157*f* is positioned on arm 157*c* and can be engaged to depress arm 157*c* and projection 157*d* to remove projection 157*d* from an opening 155*a* of arm 155 to facilitate removal of trocar 157 from center rod 154. Trocar tip 157*a* includes a throughbore 157*g* dimensioned to receive a suture (not shown) to facilitate locating and removal of trocar 157 and/or anvil assembly 30 within and from the human body. Although illustrated as having a sharpened tip, other trocar tip configurations are envisioned, e.g., a blunt tip.

FIG. 13A illustrates an alternate embodiment of the trocar shown generally as 157'. Trocar 157' differs from trocar 157 in that it further includes an elongated rib 157*h'* which is dimensioned to slide between arms 155 (FIG. 12) of center rod 154. Rib 157*h'* ensures alignment of projection 157*d'* with openings 155*a* (FIG. 12) of arms 155. Projection 157*d'* also includes a tapered or angled face 157*i'*.

Shell Assembly

Referring to FIG. 6, shell assembly 31 includes a shell 182, a pusher back 186, a cylindrical knife 188, and a staple guide 192. Shell 182 includes an outer housing portion 194 and an inner guide portion 196 having grooves 196*a* for mating with splines 181 on anvil center rod 154 (FIG. 10). Outer housing portion 194 defines a throughbore 198 having a distal cylindrical section 200, a central conical section 202 and a proximal smaller diameter cylindrical section 204. A plurality of openings 206 are formed in conical section 202. Openings 206 are dimensioned to permit fluid and tissue passage during operation of the device. A pair of diametrically opposed flexible engagement members 207 are formed on proximal cylindrical section 204 of shell 182. Engagement members 207 are positioned to be received in openings 207*a* formed on the distal end of outer tube 14*a* to secure shell 182 to elongated body 14. A pair of openings 211 formed in the proximal end of outer tube 14*a* are dimensioned to receive protrusions (not shown) formed on the internal wall of stationary handle 18 to facilitate attachment of tube 14*a* to handle portion 12.

Pusher back 186 includes a central throughbore 208 which is slidably positioned about inner guide portion 196 of shell 182. Pusher back 186 includes a distal cylindrical section 210 which is slidably positioned within distal cylindrical section 200 of shell 182, a central conical section 212 and a proximal smaller diameter cylindrical section 214. The proximal end of pusher back 186 includes members 220 which are configured to lockingly engage with resilient fingers 110 of pusher link 74 to fasten pusher link 74 to pusher back 186 such that a distal face of pusher link 74 abuts a proximal face of pusher back 186.

The distal end of pusher back 186 includes a pusher 190. Pusher 190 includes a multiplicity of distally extending fingers 226 dimensioned to be slidably received within slots 228 formed in staple guide 192 to eject staples 230 therefrom. Cylindrical knife 188 is frictionally retained within the central throughbore of pusher back 186 to fixedly secure knife 188 in relation to pusher 190. Alternately, knife 188 may be retained within pusher back 186 using adhesives, crimping, pins, etc. The distal end of knife 188 includes a circular cutting edge 234.

In operation, when pusher link 74 is advanced distally in response to actuation of firing trigger 20, as will be described below, pusher back 186 is advanced distally within shell 182. Advancement of pusher back 186 advances fingers 226 through slots 228 of staple guide 192 to advance staples 230 positioned within slots 228 and eject staples 230 from staple guide 192 into staple deforming pockets 140 of anvil 129. Since knife 188 is secured to pusher back 186, knife 188 is also advanced distally to core tissue as will be described in more detail below.

Figure 14:
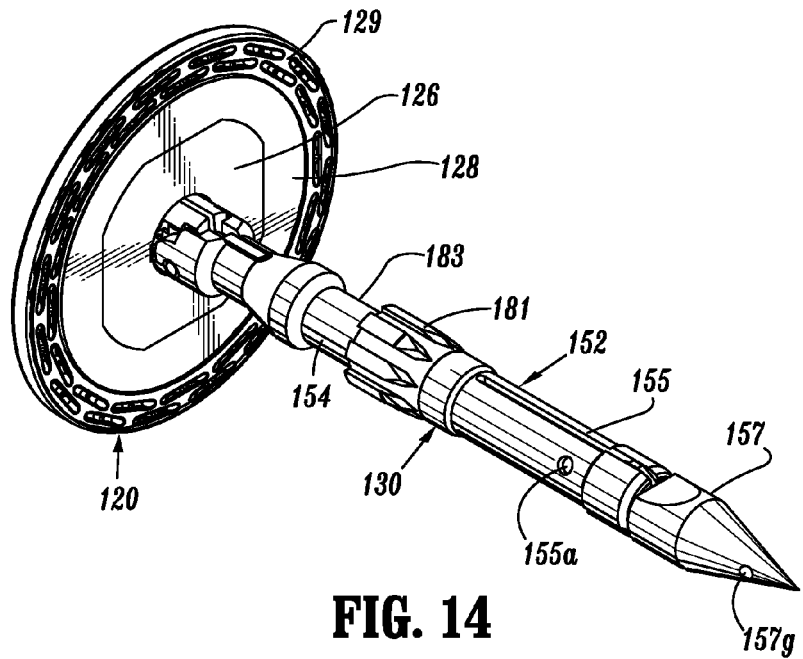
FIG. 14 is a side perspective view from the proximal end of the anvil assembly shown in FIG. 10 with the removable trocar attached thereto.
Figure 15:
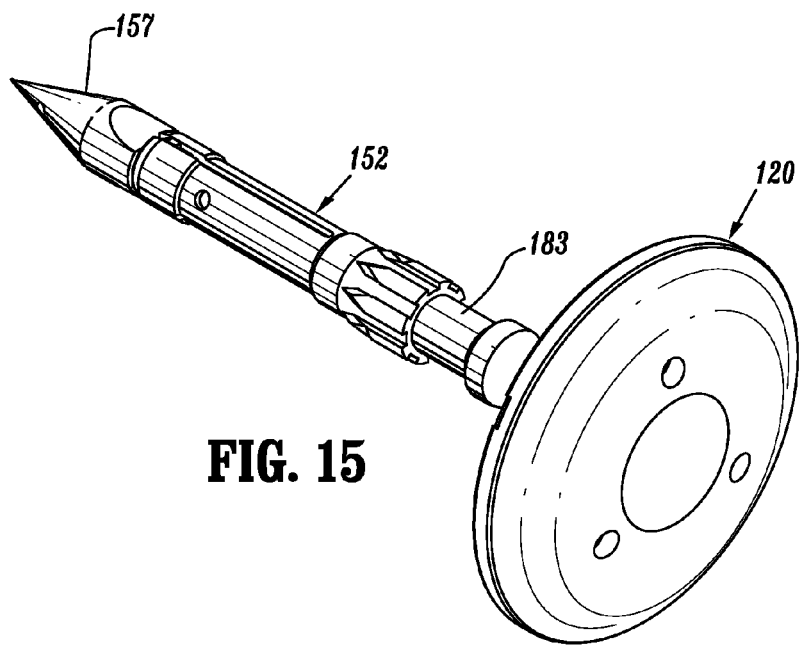
FIG. 15 is a side perspective view from the distal end of the anvil assembly shown in FIG. 14.
Figure 16:
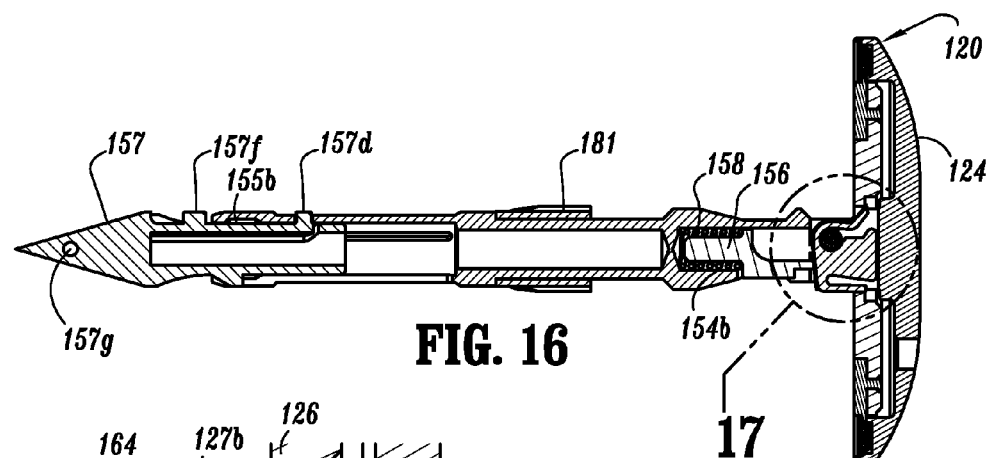
FIG. 16 is a side cross-sectional view taken through the retaining clip of the anvil assembly and removable trocar of the anvil assembly shown in FIG. 15.

A rigid bushing 209 is supported in the proximal end of inner guide portion 196 of shell 182. Bushing 209 defines a throughbore dimensioned to slidably receive anvil retainer 38 and center rod 154 of anvil assembly 30 (FIG. 14). Bushing 209 provides lateral support for flexible arms 155 of center rod 154 when the anvil assembly 30 has been approximated to prevent disengagement of anvil assembly 30 from anvil retainer 38. More specifically, when flexible arms 155 are positioned within bushing 209, bushing 209 prevents flexible arms 155 of center rod 154 of anvil assembly 30 from flexing outwardly to prevent disengagement of anvil assembly 30 from annular rib 177 of anvil retainer 38. In the unapproximated position, flexible arms 155 of center rod 154 are positioned externally of bushing 209 to permit removal of anvil assembly 30 from retainer 38.

As discussed above, dwell 50*a* in channel 50 of screw 32 can be located on screw 32 to provide an indication to a surgeon that the anvil assembly 30 has been unapproximated a distance sufficient to allow removal of anvil assembly 30 from anvil retainer 38 or, alternatively, that any further unapproximation of anvil assembly 30 will move anvil assembly 30 to a position in which anvil assembly 30 can be disengaged from anvil retainer 38. As such, when a surgeon is rotating approximation knob 22 to unapproximate anvil assembly 30 and shell assembly 31, a tactile indication is provided to the surgeon by dwell 50*a* in channel 50 of screw 52 to indicate to the surgeon that anvil assembly has been unapproximated to one of the positions described above.

Cam Adjustment Mechanism

Referring to FIGS. 8 and 22-28, a cam adjustment member 400 is secured by set screw 312 onto a sidewall 306*a* of screw stop 306 within a recess 306*b* formed in sidewall 306*a*. Cam adjustment member 400 includes a circular disc 402 having a throughbore 404. Throughbore 404 is eccentrically formed through disc 402 and is dimensioned to receive set screw 312. A smaller notch or hole 406 is also formed in disc 402 and is dimensioned to receive the tip of an adjustment tool (not shown). Recess 306b (FIG. 22) includes a forward abutment shoulder or surface 306c and a rear abutment surface 306d and is dimensioned to receive disc 402 such that the outer edge of disc 402 abuts forward and rear abutment surfaces 306c and 306d.

Set screw 312 extends through disc 402 and screw stop 306 and is received in a threaded bore 32a (FIG. 6) in screw 32 to secure screw stop 306 in an axially fixed position on screw 32. Cam adjustment member 400 functions to adjust the axial position of screw stop 306 on screw 32. More specifically, set screw 312 can be loosened to allow disc 402 to rotate within recess 306b of screw stop 306. Since disc 402 is eccentrically mounted about screw 32 and engages forward and rear abutment surfaces 306c and 306d of recess 306b, rotation of disc 402 about fixed set screw 312 will urge screw stop 306 axially along screw 32 to adjust the axial position of screw stop 306 on screw 32. For example, when disc 402 is rotated in a clockwise direction (as viewed in FIG. 28) as indicated by arrow "B", screw stop 306 will be moved axially in relation to screw 32 in the direction indicated by arrow "C" in response to engagement between the outer edge of disc 402 and rear shoulder 306d of recess 306b. Conversely, when disc 402 is rotated in a counter-clockwise direction (as viewed in FIG. 27), as indicated by arrow "D", screw stop 306 will be moved axially in relation to screw 32 in the direction indicated by arrow "E" in response to engagement between the outer edge of disc 402 and forward shoulder 306c of recess 306b.

When stapling device 10 is in a fully approximated position, i.e., anvil assembly 30 and shell assembly 31 are brought into juxtaposed alignment to define a tissue receiving clearance (FIG. 46), screw stop 306 abuts against body portion 42 of the rotatable sleeve 33, i.e., sleeve 33 functions as a stop for the approximation mechanism. See FIG. 48. In this position, anvil assembly 30 and shell assembly 31 are spaced slightly to define a tissue receiving clearance. By providing cam adjustment member 400, the tissue receiving clearance can be selectively adjusted to be within a desired range by adjusting the position of screw stop 306 on screw 32. Preferably, cam adjustment member 400 permits adjustment of the tissue receiving clearance of ±0.045 inches, although greater or lesser adjustment capabilities are also envisioned. Typically, adjustments to the tissue receiving clearance will be made by the device manufacturer. Alternately, a hole or opening may be provided in handle portion 12 (FIG. 1) to provide direct access to adjustment member 400 to allow for on-site adjustment of the tissue receiving clearance by a surgeon or other medical professional.

Indicator Mechanism

Figure 32:
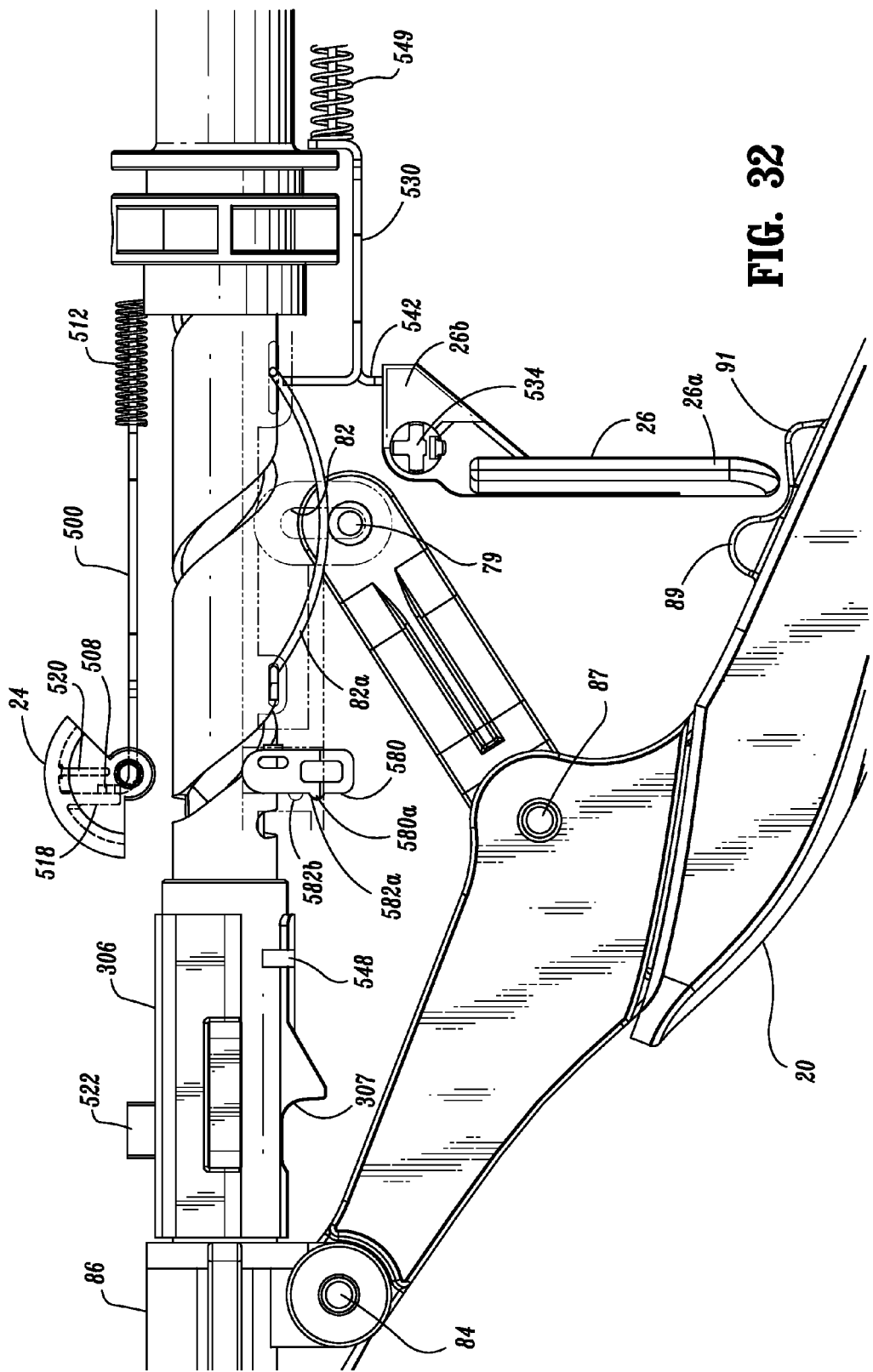
FIG. 32 is a side enlarged view of the handle assembly of the surgical stapling device shown in FIG. 31 with the handle sections removed.

Referring to FIGS. 3-5 and 29, the indicator mechanism includes bulbous indicator 24, lens cover 24a and slide member 500. Indicator 24 is pivotally supported about a pivot member 502 which is preferably formed monolithically with handle sections 18a and 18b. Lens cover 24a is positioned above indicator 24 and is preferably formed of magnification material to facilitate easy visualization of indicator 24. Slide member 500 includes a body portion 504 having a elongated slot 506 formed therein, a distal abutment member or upturned lip portion 508, and a proximal extension 510. Slide member 500 is slidably positioned between handle sections 18a and 18b. Proximal extension 510 is slidably supported within stationary handle 18 by support structure 516 (FIG. 5) which may be integrally formed with handle sections 18a and 18b. A biasing member, preferably a coil spring 512, is positioned in compression about proximal extension 510 between support structure 516 and body portion 504 of slide member 500 to urge slide member 500 distally within stationary handle 18. Indicator 24 includes a pair of downwardly extending projections 518 and 520 (FIG. 32). Upturned lip portion 508 of slide member 500 is positioned between projections 518 and 520 and is positioned to engage projections 518 and 520 as it moves within stationary handle 18. In the unfired position of device 10, biasing member 512 urges slide member 500 distally to move lip portion 508 into engagement with projection 518 to pivot indicator to a first position, which provides indication to a surgeon that the device has not been approximated and is not in a fire-ready condition.

Figure 33:
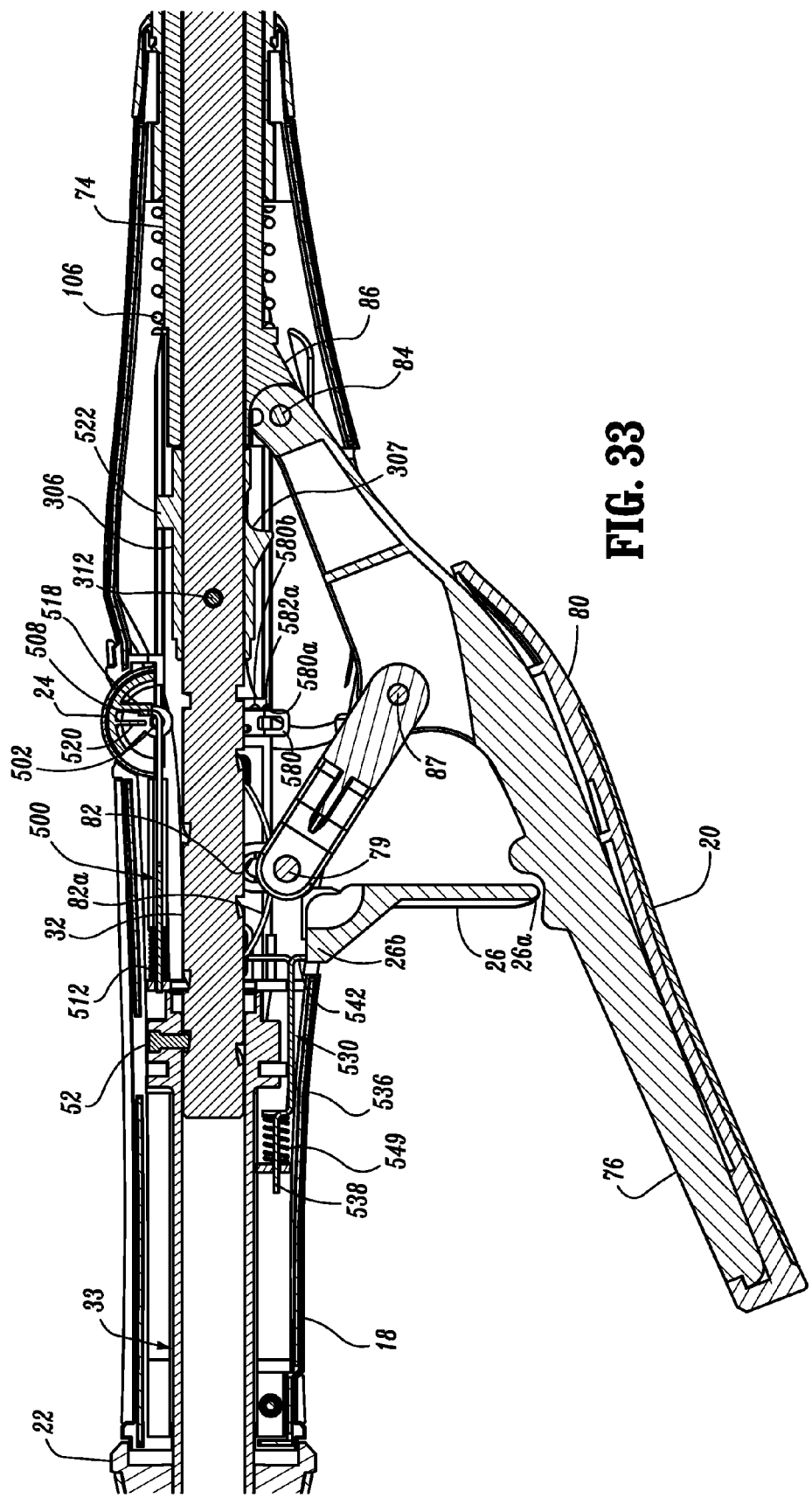
FIG. 33 is an enlarged view of the indicated area of detail shown in FIG. 31.
Figure 34:
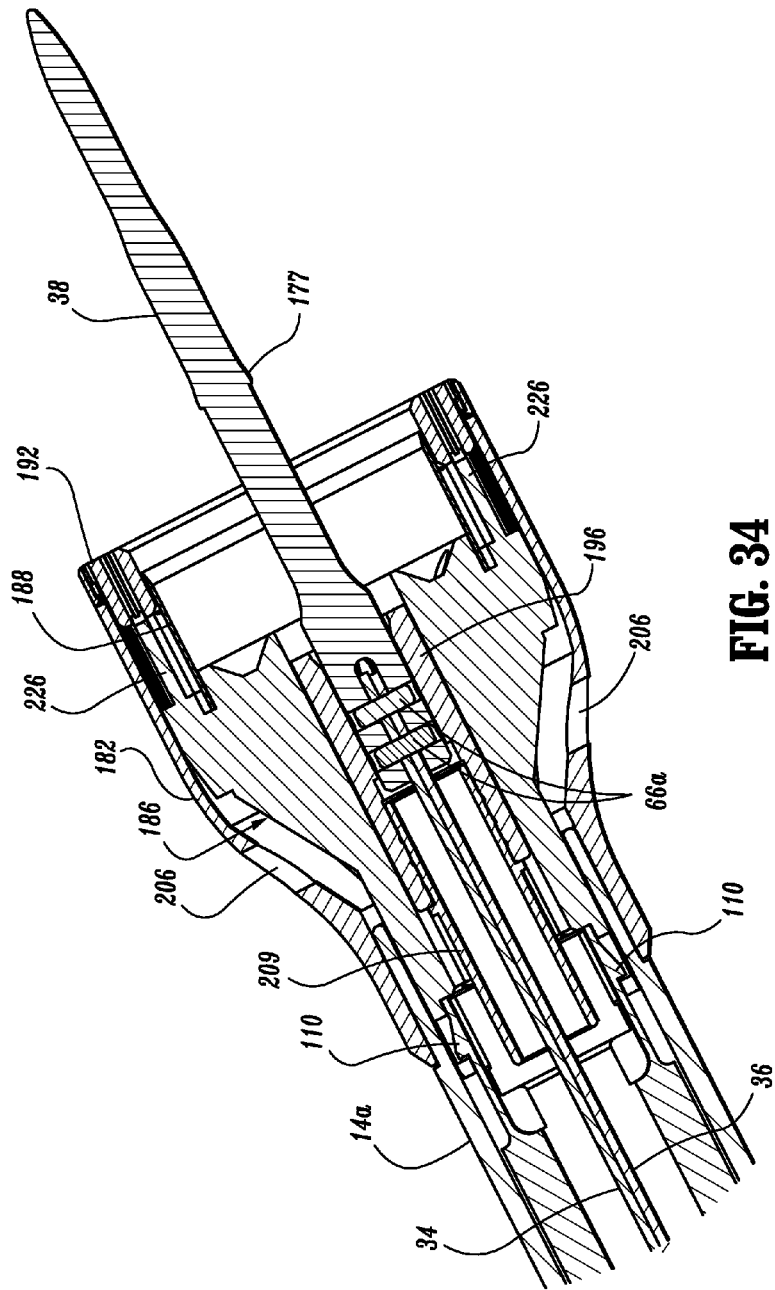
FIG. 34 is an enlarged view of the indicated area of detail shown in FIG. 31.
Figure 35:
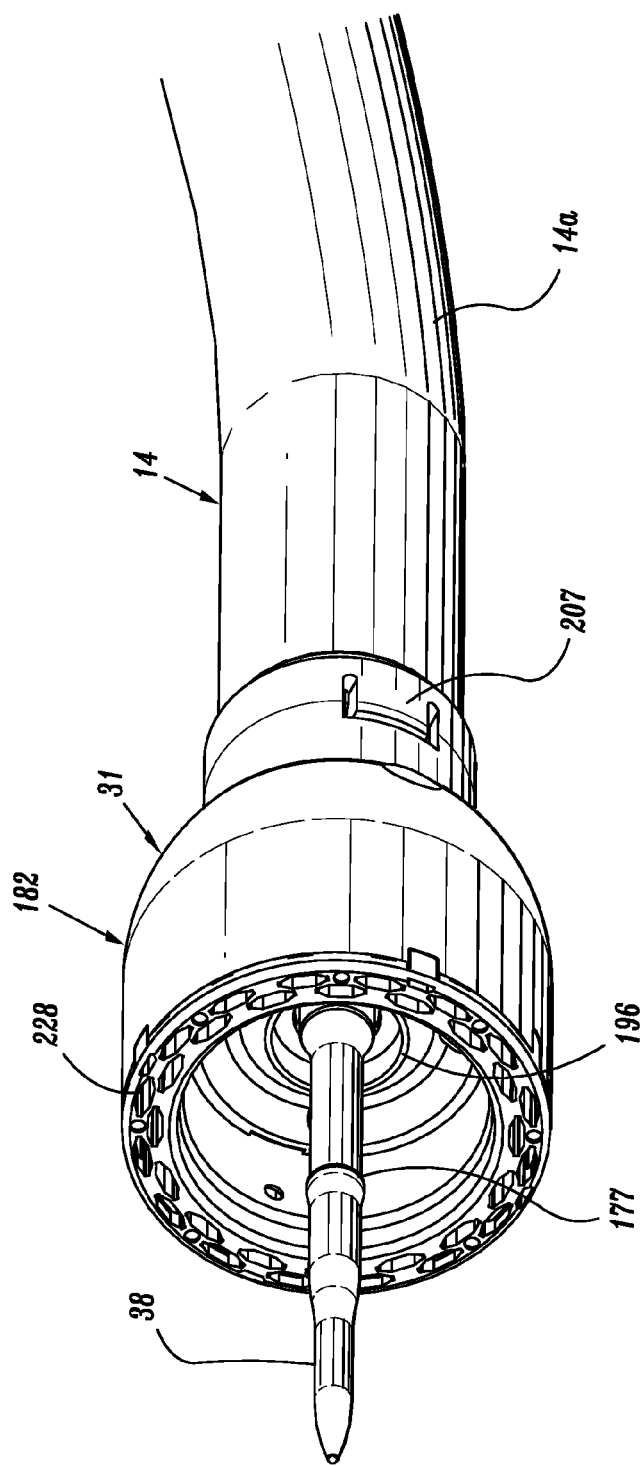
FIG. 35 is a perspective view from the front of the distal end of the surgical stapling device shown in FIG. 31 with the anvil assembly removed.
Figure 36:
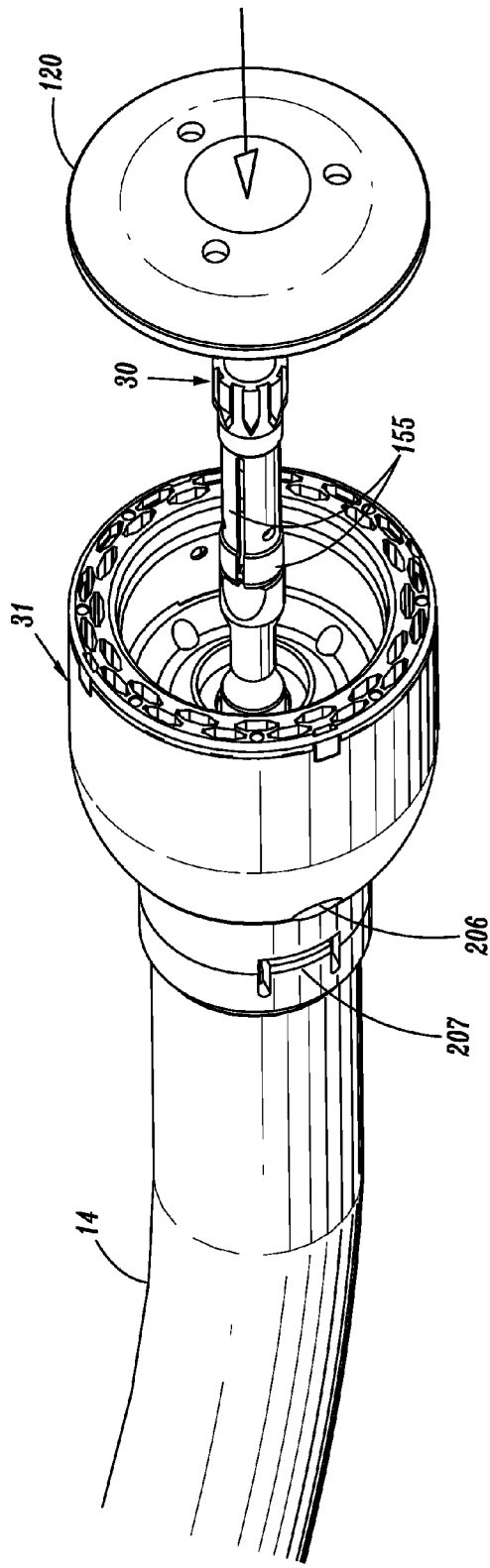
FIG. 36 is a perspective view from the front of the distal end of the surgical stapling device shown in FIG. 35 with an anvil assembly attached thereto.

As discussed above, screw stop 306 is fixedly attached to screw 32 (FIG. 33). Screw stop 306 includes a first abutment or engagement member 522 which is positioned to travel through slot 506 of slide member 500 and engage the proximal end 506a (FIG. 29) of slot 506 during approximation of the device. When engagement member 522 abuts proximal end 506a of slot 506, further approximation of device 10 moves slide plate 500 proximally within stationary handle 18 against the bias of spring 512 such that upturned lip 508 of slide member 500 engages projection 520 of indicator 24. Engagement between projection 520 and lip 508 causes indicator 24 to pivot about pivot member 502 to a second position. In the second position, indicator 24 provides indication to a surgeon that the device has been approximated and is now in a fire-ready position. See FIG. 48.

Fire-Lockout Mechanism

Referring to FIGS. 3-5, and 30, the firing-lockout mechanism includes trigger lock 26 and a lockout member 530. Trigger lock 26 is pivotally supported within bores 532 (FIG. 3) in handle sections 18a and 18b about pivot member 534. Pivot member 534 is preferably T-shaped and frictionally engages the inner wall of bores 532 to prevent free rotation of trigger lock 26. Alternately, other pivot member configurations are envisioned, e.g., circular, square, etc. Tip 26a of trigger lock 26 is positioned between abutments 89 and 91 on body portion 76 of firing trigger 20 to prevent actuation of trigger 20 when trigger lock 26 is in the locked position. Trigger lock 26 also includes a proximal extension 26b which will be discussed in further detail below.

Referring also to FIG. 3B, an alternate embodiment of the trigger lock is shown generally as 26'. Trigger lock 26' includes a flexible extension or tab 26b' which extends outwardly from tip 26a'. Extension 26b' is dimensioned to engage the space between abutments 89 and 91 to prevent rattling of trigger lock 25' between abutments 89 and 91. Flexible extension 26b' is deformable to facilitate passage over abutment 91.

Lockout member 530 includes a body portion 536, a proximal extension 538, a pair of front legs 540a, a pair of rear legs 540b, and an abutment member or downturned lip portion 542. Lockout member 530 is slidably positioned between first and second stops 544 and 546 (FIG. 5) formed on an internal wall of handle sections 18a and 18b. Stop 544 is positioned to engage rear legs 540b and stop 546 is positioned to engage front legs 540a. It is also envisioned that a single abutment member may be substituted for each pair of legs. A biasing member, preferably a coil spring 549, is positioned between stop 544 and body 536 about proximal extension 538 to urge lockout 530 to its distal-most position with legs 540 abutting stop 546. In this position, extension 26*b* of trigger lock 26 is positioned beneath lip portion 542 of lockout member 530 to prevent pivotal movement of trigger lock 26 about pivot member 534, and thus prevent firing of stapling device 10.

Figure 23:
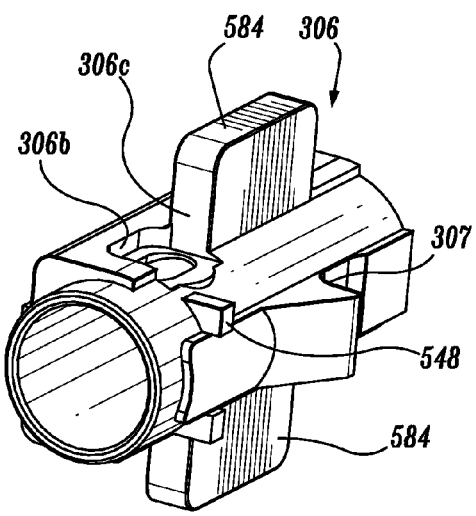
FIG. 23 is a bottom perspective view from the proximal end of the screw stop shown in FIG. 22.
Figure 24:
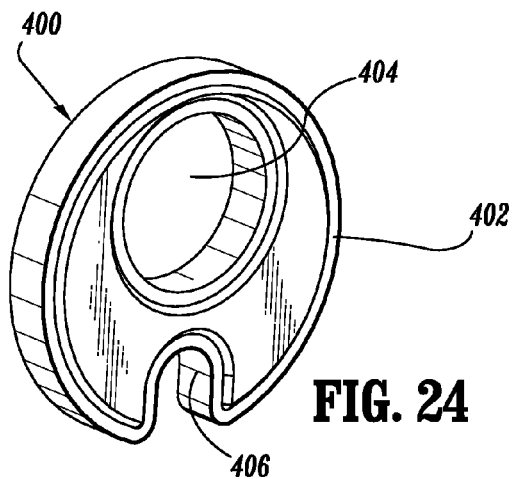
FIG. 24 is a top perspective view of the cam adjustment member of the handle assembly shown in FIG. 3.
Figure 25:
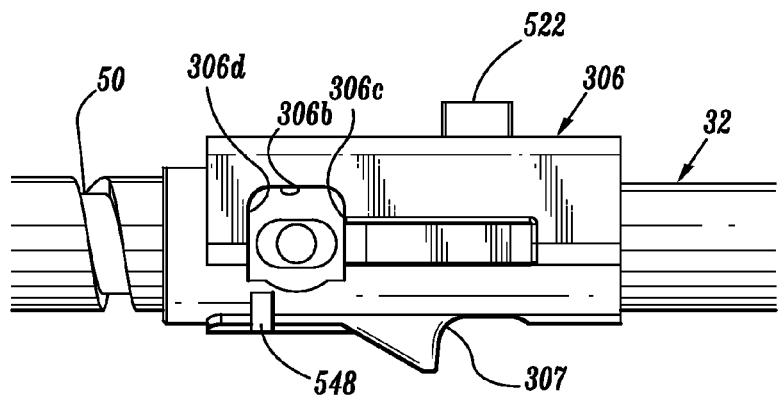
FIG. 25 is a side view of the screw and screw stop of the handle assembly shown in FIG. 3 with the set screw and the cam adjustment member removed.
Figure 26:
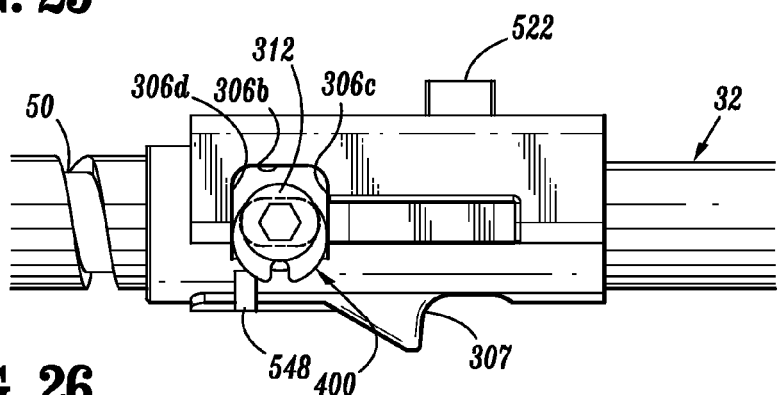
FIG. 26 is a side view of the screw and screw stop shown in FIG. 25 with the set screw and cam adjustment member attached thereto.
Figure 27:
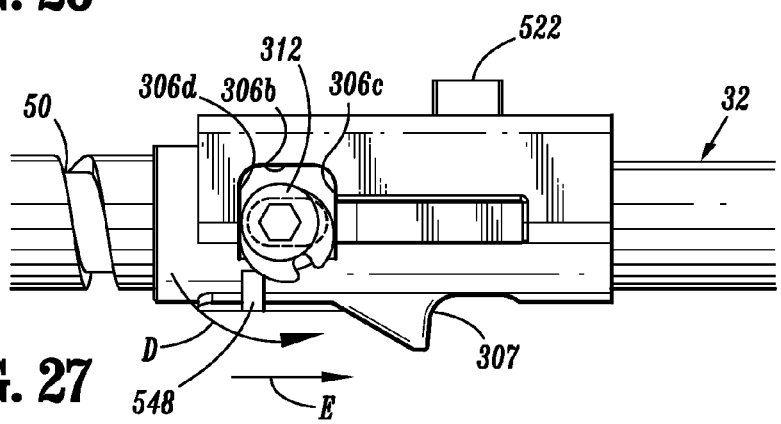
FIG. 27 is a side view of the screw and screw stop shown in FIG. 26 with the cam adjustment screw adjusted to increase the tissue gap.
Figure 28:
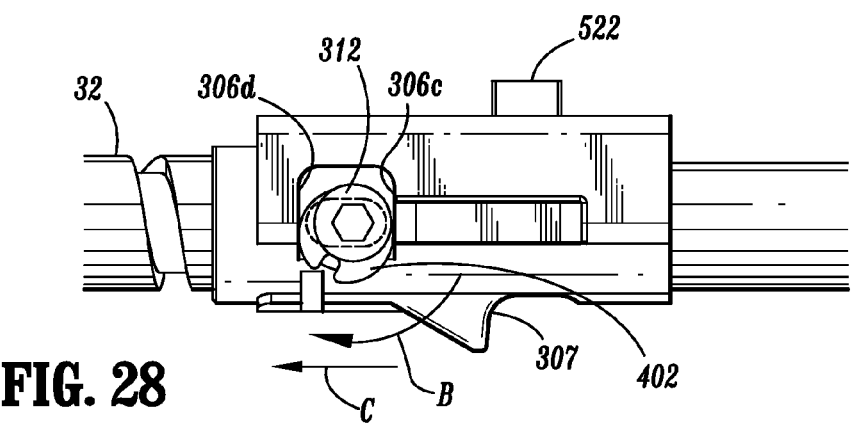
FIG. 28 is a side view of the screw and screw stop shown in FIG. 26 with the cam adjustment screw adjusted to decrease the tissue gap.
Figure 29:
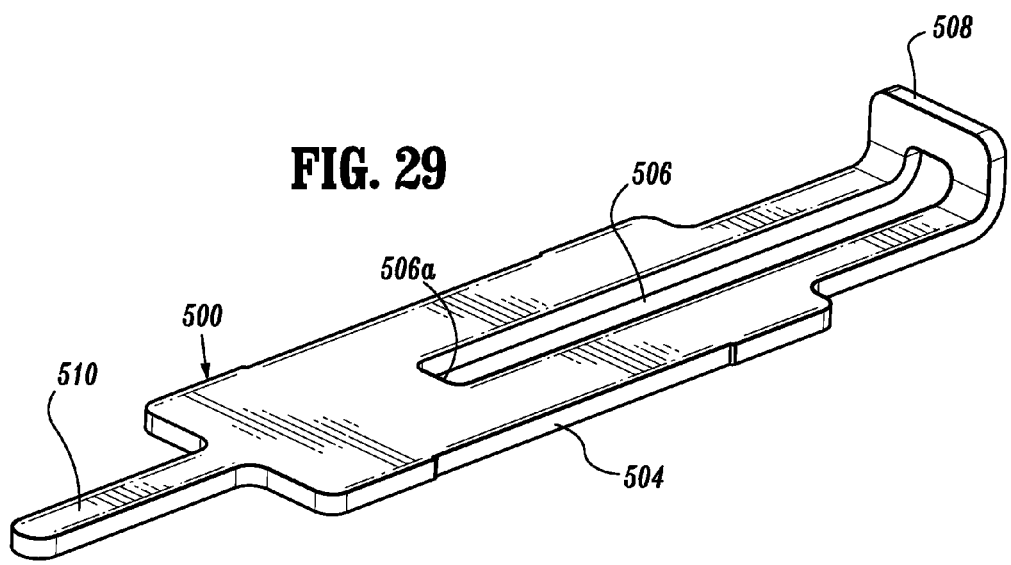
FIG. 29 is a top perspective view from the proximal end of the slide member of the indicator mechanism of the handle assembly shown in FIG. 3.
Figure 30:
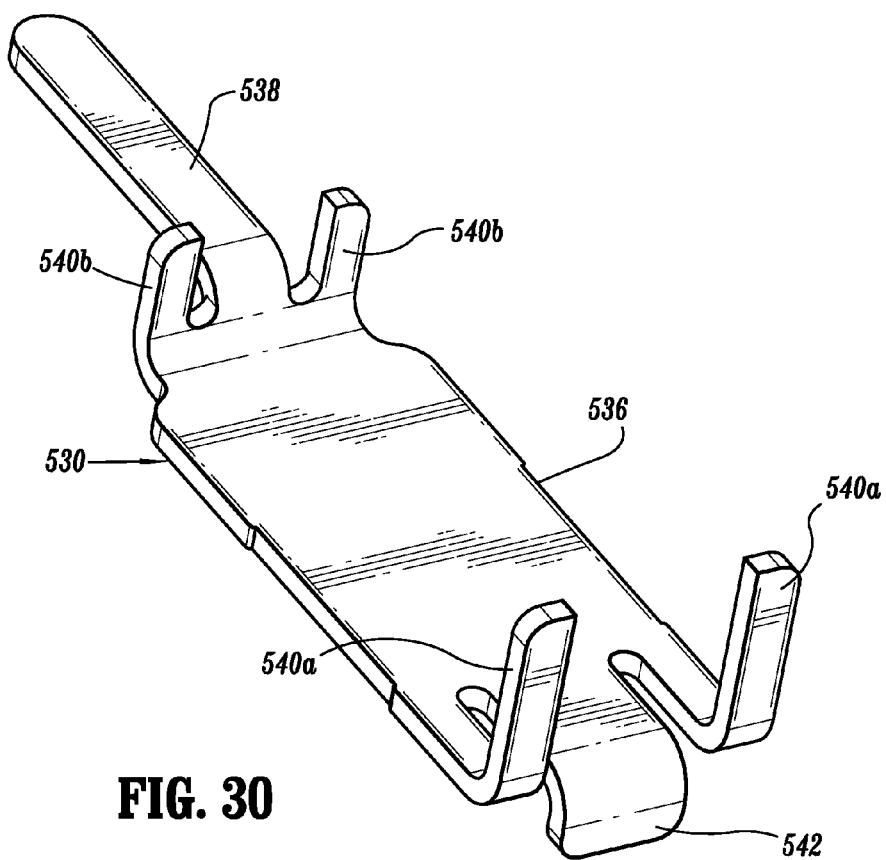
FIG. 30 is a bottom perspective view of the lockout member of the fire lockout mechanism of the handle assembly shown in FIG. 3.
Figure 31:
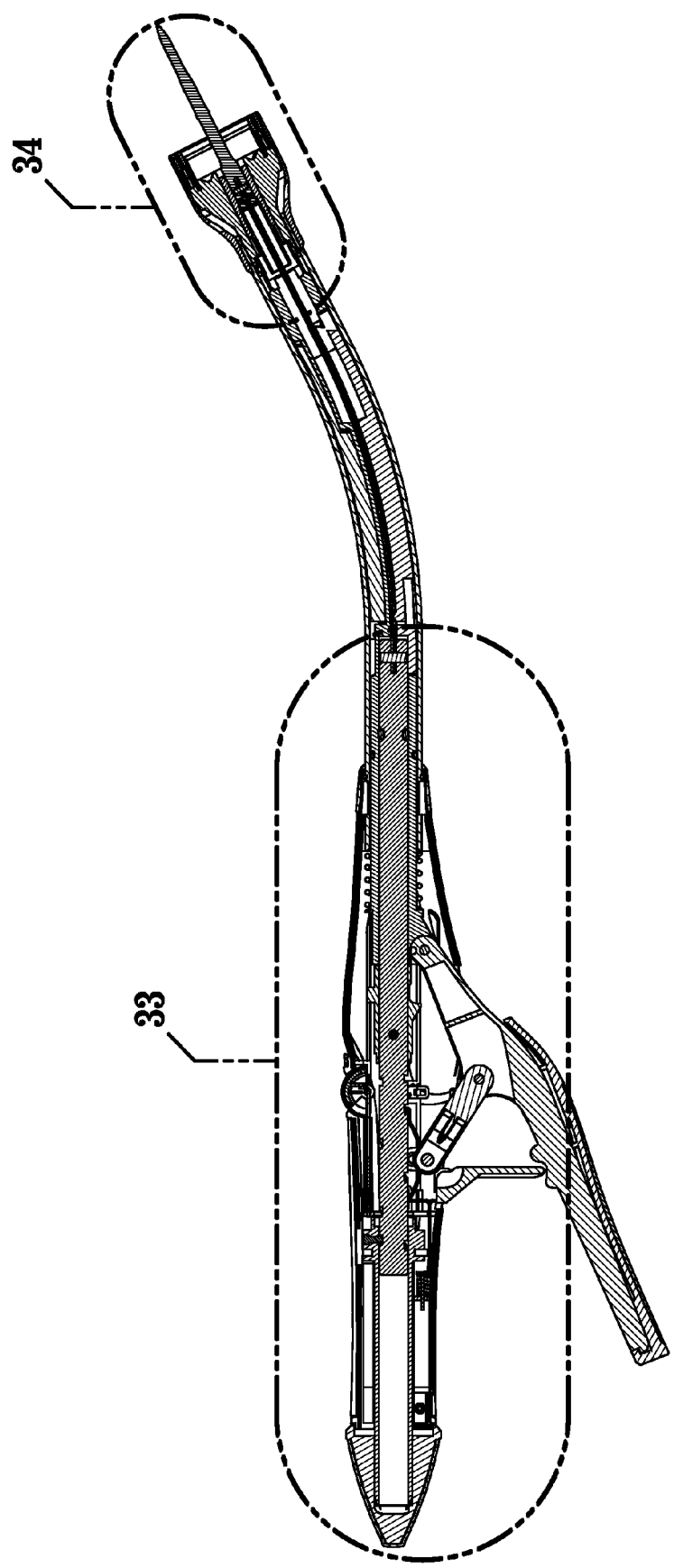
FIG. 31 is a side cross-sectional view of the surgical stapling device shown in FIG. 1 with the anvil assembly removed.

As discussed above, screw stop 306 is secured to screw 32. A second engagement member or members 548 extend downwardly from screw stop 306 (FIG. 23). When stapling device 10 is approximated and screw 32 is moved proximally within stationary handle 18, engagement member 548 abuts distal legs 540*a* (FIG. 47) of lockout member 530 to move lockout member 530 proximally against the bias of spring member 549 to a position in which lip portion 542 is spaced proximally of extension 26*b* of trigger lock 26. In this position of lockout member 530, trigger lock 526 can be pivoted about pivot member 534 to permit firing of stapling device 10.

Tactile Indicator Mechanism

Referring to FIGS. 3, 5, 9 and 9A, a tactile indicator mechanism provided in stationary handle 18 includes an abutment member 580 which is slidably positioned in a vertical slot 582 defined within handle sections 18*a* and 18*b*. Abutment member 580 includes a protuberance 580*a* and a guide rib 580*b*. Protuberance 580*a* is dimensioned to be received within one of two detents 582*a* and 582*b* formed along a wall of slot 582. Abutment member 580 is movable from a retracted (downward) position, wherein protuberance 580*a* is positioned within detent 582*a*, to an extended (upward) position, wherein protuberance 580*a* is positioned within detent 582*b*. Engagement between protuberance 580*a* and detents 582*a* and 582*b* retains abutment member 580 in its respective upward or downward position.

Prior to firing of stapling device 10, abutment member 580 is located in the retracted (downward) position. When device 10 is fired, an extension 590 (FIG. 3) of firing link 72 engages abutment member 580 and moves abutment member 580 from its retracted to its extended position. In the extended position, abutment member 580 extends into channel 111 of stationary handle 18.

Screw stop 306 includes a pair of wings 584 which are slidably positioned in channel 111 of stationary handle 18. After stapling device 10 has been fired, abutment member 580 is positioned within channel 111. During unapproximation of anvil assembly 30 and cartridge assembly 31, a wing 584 of screw stop 306 will engage abutment member 580 and urge abutment member 580 back to its retracted (downward) position. Engagement between abutment member 580 and wing 584 of screw stop 306 provides a tactile and/or an audible indication to the surgeon that the anvil and cartridge assemblies 30 and 31 have been unapproximated a predetermined amount. Preferably, abutment member 580 is positioned to engage wing 584 of screw stop 306 at the point when the anvil and cartridge assemblies have been separated a distance sufficient to allow the anvil head assembly to tilt. Thus, engagement between abutment member 580 and wing 584 of screw stop 306 provides a tactile and/or audible indication to the surgeon that the anvil head assembly 120 has tilted and stapling device 10 can be removed from a patient.

Operation

Operation of surgical stapling device 10 will now be described in detail with reference to FIGS. 31-61.

FIGS. 31-35 illustrate surgical stapling device 10 in the unapproximated or open position prior to attachment of anvil assembly 30 to anvil retainer 38. In this position, biasing member 106 (FIG. 33) is engaged with coupling 86 to urge pusher link 74 to its proximal-most position in which coupling 86 abuts screw-stop 306. Biasing member 512 is engaged with slide member 500 of the indicator mechanism to position slide member 500 in engagement with projection 518 of indicator 24 to pivot indicator 24 in a clockwise direction, as viewed in FIG. 33. Biasing member 549 is engaged with body 536 of lockout member 530 to urge lockout member 530 to its distal-most position, wherein lip portion 542 of lockout member 530 is positioned above extension 26*b* of trigger lock 26 to prevent movement of trigger lock 26 to the unlocked position. Biasing member 82*a* is also engaged with pivot member 79 (FIG. 32) to urge pivot member 79 to the base of vertical slot 82 and tactile indicator 580 is in the retracted or downward position with protrusion 580*a* positioned with detent 582*a*.

Figure 37:
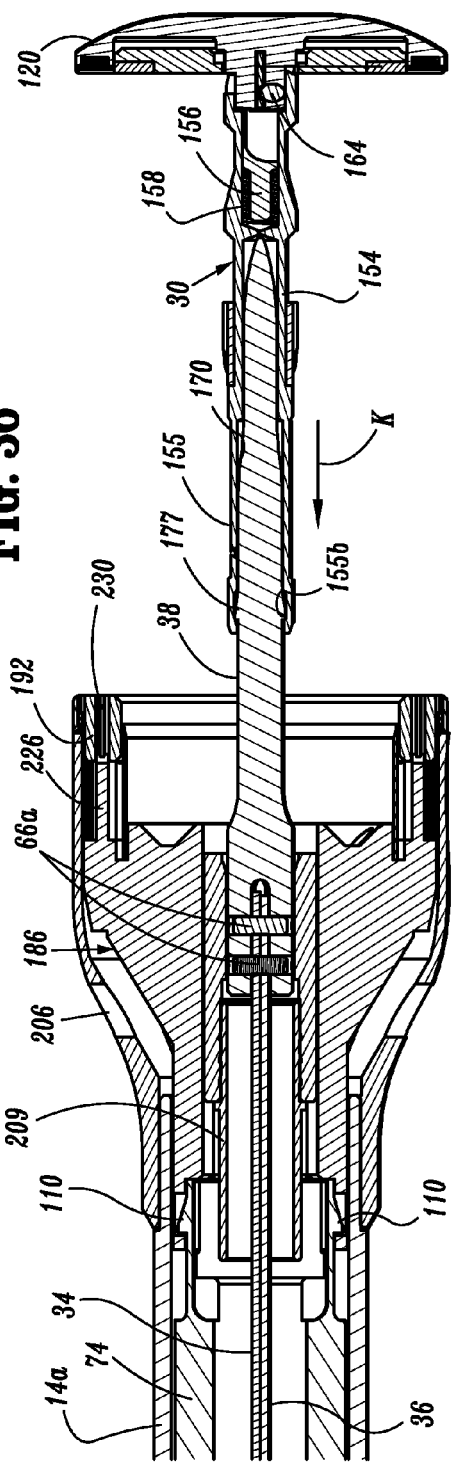
FIG. 37 is a side cross-sectional view of the distal end of the surgical stapling device shown in FIG. 36.
Figure 38:
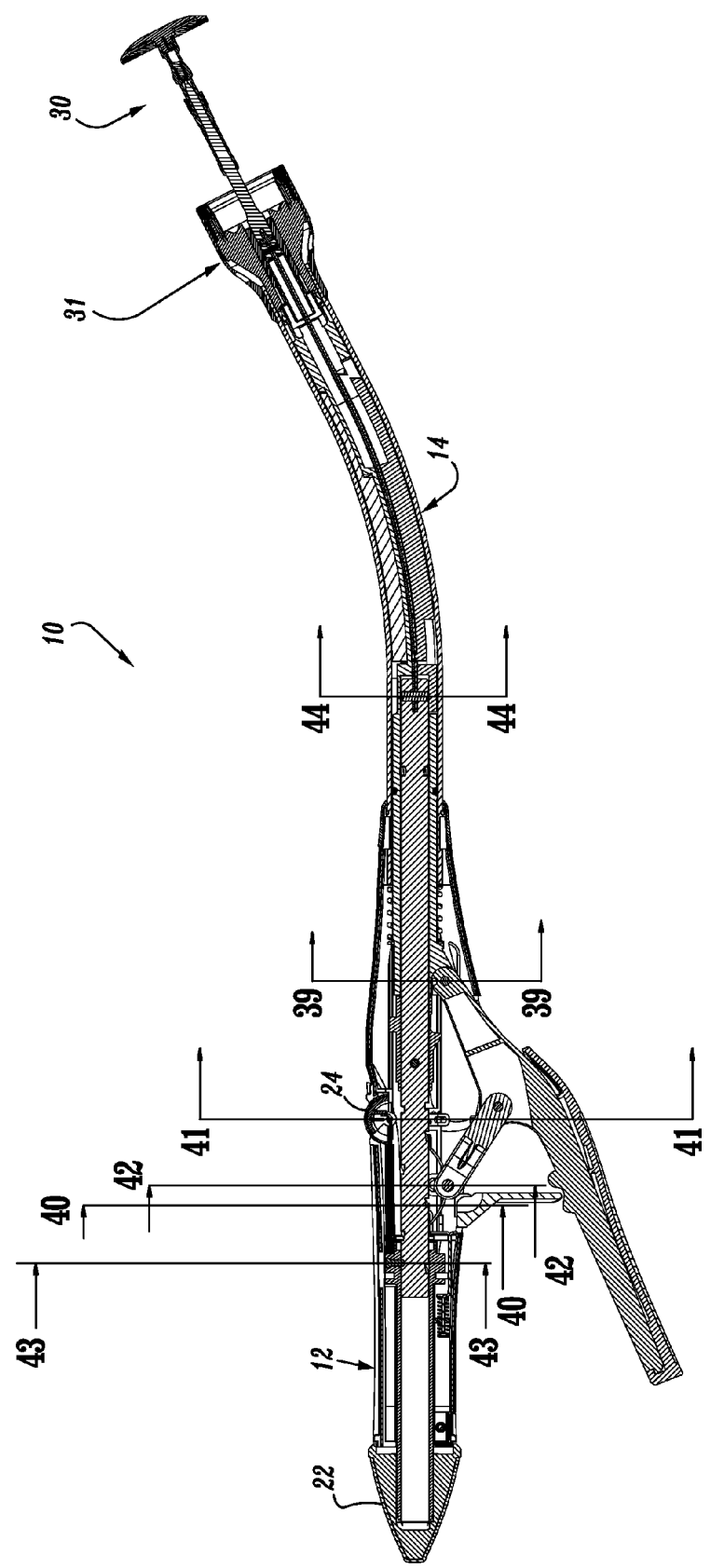
FIG. 38 is a side cross-sectional view of the surgical stapling device shown in FIG. 31 with the anvil assembly attached thereto.
Figure 45:
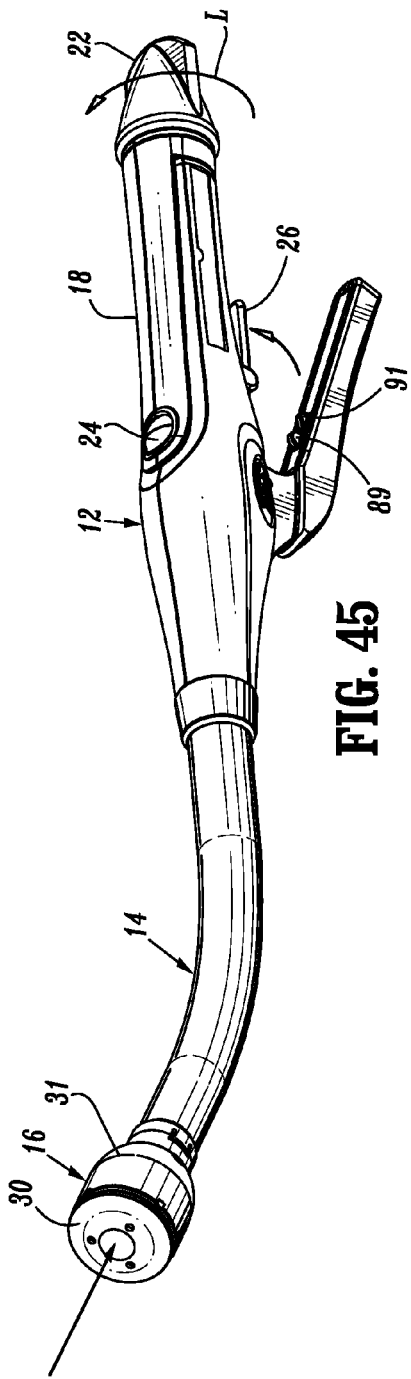
FIG. 45 is a side perspective view of the surgical stapling device shown in FIG. 38 with the anvil assembly in an approximated position.

FIGS. 36-44 illustrate surgical stapling device 10 with anvil assembly 30 attached to anvil retainer 38 and the anvil assembly 30 in the unapproximated or open position. Referring to FIGS. 37 and 38, during attachment of anvil assembly 30 to anvil retainer 38, anvil retainer 38 is positioned within bore 170 of center rod 154 of anvil assembly 30. Flexible arms 155 deflect outwardly to accommodate center rod 154. Center rod 154 is advanced onto anvil retainer 38 in the direction indicated by arrow "K" in FIG. 37 until internal shoulder 155*b* of flexible arms 155 passes over annular protrusion 177 formed on anvil retainer 38. At this point, resilient legs 155 releasably engage the anvil retainer. The position of the remaining components of stapling device are not affected by attachment of anvil assembly 30 to anvil retainer 38 and remain as described above and shown in FIGS. 31-35.

Figure 46:
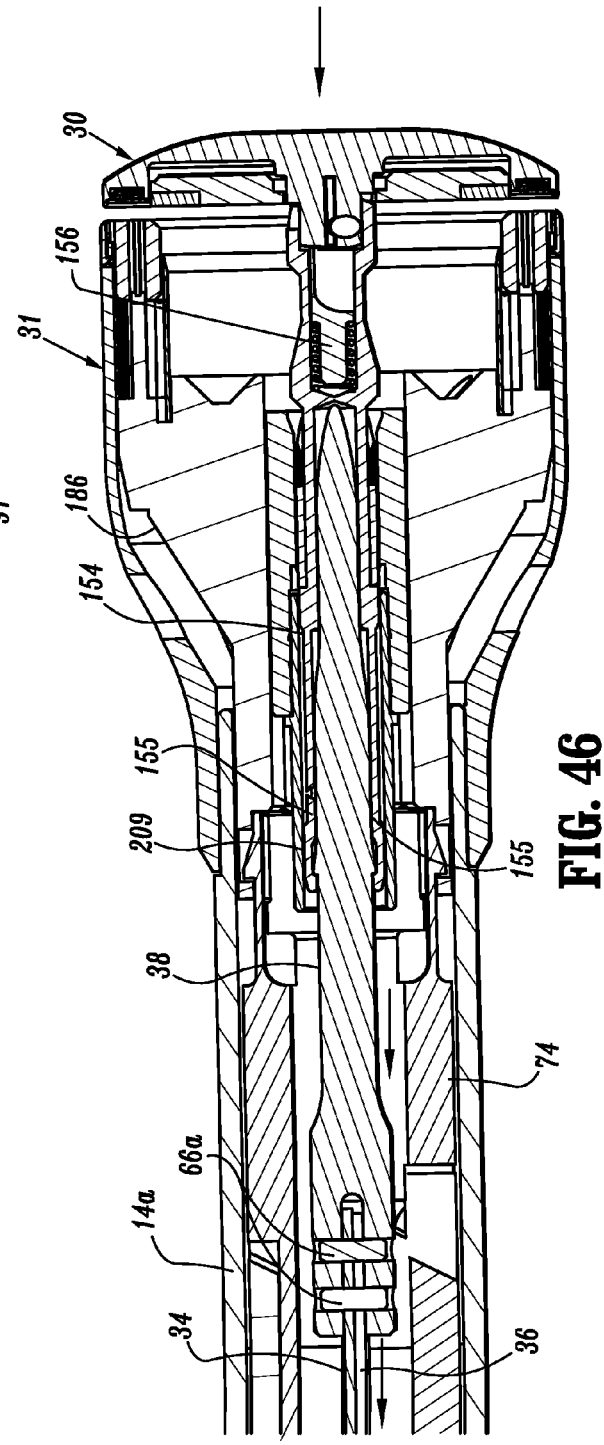
FIG. 46 is a side cross-sectional view of the distal end of the surgical stapling device shown in FIG. 45.

FIGS. 45-50 illustrate surgical stapling device 10 during movement of anvil assembly 30 and cartridge assembly 31 to the approximated or closed position. As discussed above, anvil assembly 30 is moved to the approximated or closed position by rotating rotation knob 22 in the direction indicated by arrow "L" in FIG. 45. Rotation of knob 22 causes cylindrical sleeve 33 to rotate to move pin 52 along helical channel 50 of screw 32. See FIG. 48. Movement of pin 52 along helical channel 50 causes screw 32 to translate proximally within sleeve 33. The distal end of screw 32 is connected to screw extensions 34 and 36 which are fastened at their distal ends to anvil retainer 38 (FIG. 46). As such, retraction of screw 32 within sleeve 33 is translated into proximal movement of anvil retainer 38 and anvil assembly 30. It is noted that when anvil assembly 30 is approximated, flexible legs 155 of center rod 154 are drawn into bushing 209 to lock legs 155 onto anvil retainer 38.

Figure 47:
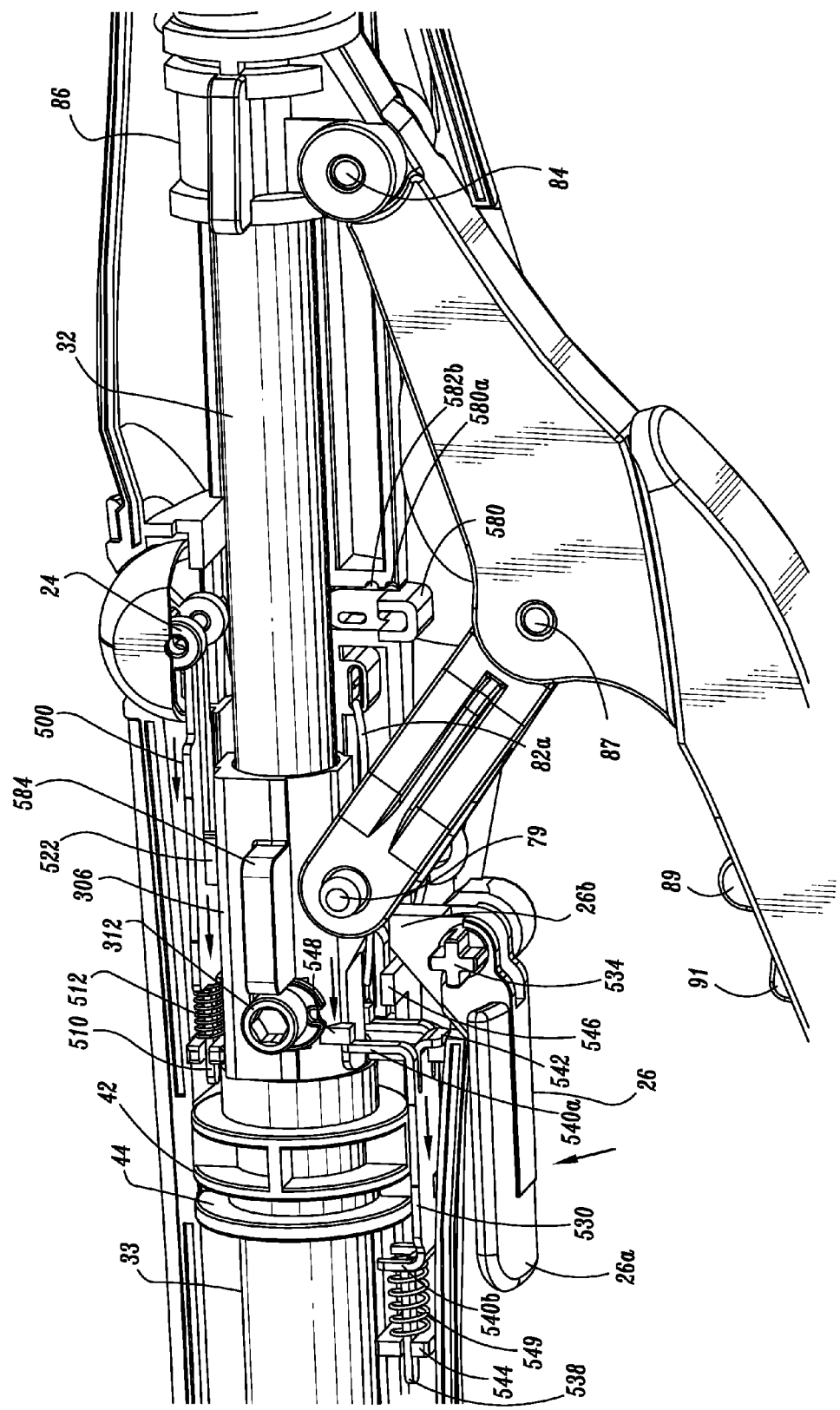
FIG. 47 is a side enlarged view of the handle assembly of the surgical stapling device shown in FIG. 45 with a handle section removed.
Figure 50:
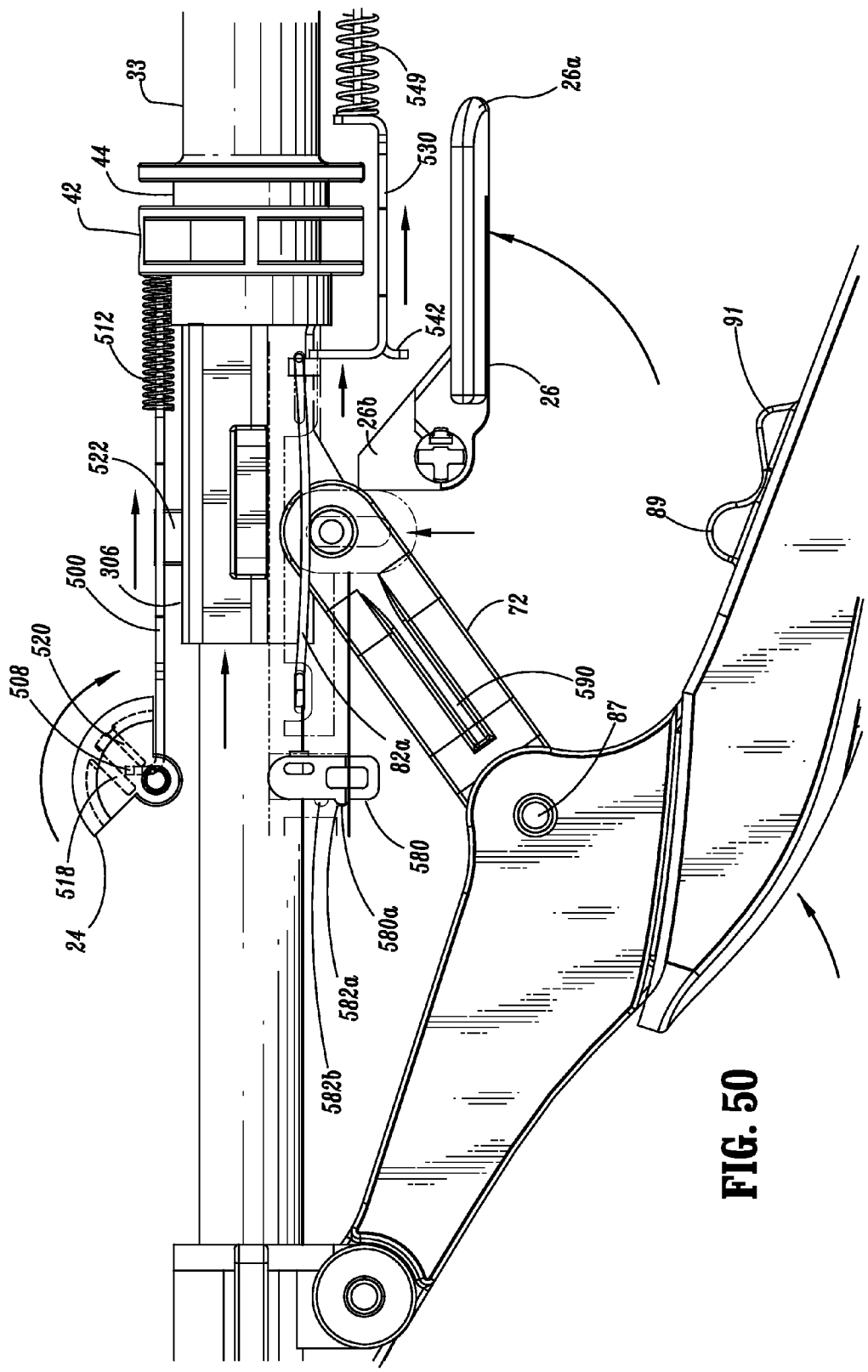
FIG. 50 is a side view of a portion of the handle assembly of the surgical stapler shown in FIG. 45 with the handle sections removed.

Referring to FIGS. 47-49, screw stop 306 is axially fixed to screw 32 by set screw 312. Thus, as screw 32 is retracted within sleeve 33, screw stop 306 is moved from a distal position within stationary handle 18 to a proximal position. As screw stop 306 moves from the distal position to the proximal position, first engagement member 522 formed on screw stop 306 abuts proximal end 506*a* of slot 506 of slide plate 500 (FIG. 29) and moves slide plate 500 proximally against the bias of spring 512. As slide plate 500 moves proximally, lip 508 (FIG. 48) of slide member 500 engages projection 520 of indicator 24 to pivot indicator 24 in a counter-clockwise direction as viewed in FIG. 48.

Screw stop 306 also includes a second engagement member 548 (FIG. 47). As screw stop 306 is moved from the distal position to the proximal position during approximation of anvil assembly 30, second engagement member 548 engages distal legs 540*a* of lockout member 530 to move lockout member 530 proximally to a position in which lip portion 542 is spaced proximally of extension 26*b* of trigger lock 26. In this position, trigger lock 26 can be pivoted to an unlocked position to permit firing of stapling device 10.

Movement of screw stop 306 to its proximal-most position within stationary handle 18 positions abutment surface 307 of screw stop 306 in position to engage pivot member 79 of firing link 72. Abutment surface 307 comprises a substantially concave surface which is positioned to partially capture and act as a backstop for pivot 79 during firing of the stapling device.

FIGS. 51-56 illustrate surgical stapling device 10 during the firing stroke of firing trigger 20. As trigger 20 is compressed towards stationary handle 18 in the direction indicated by arrow "M" in FIG. 52, pivot member 79 engages abutment surface 307 on screw stop 306 and firing trigger 20 is pushed distally. As discussed above, the distal end of firing trigger 22 is connected through coupling member 86 to the proximal end of pusher link 74. Accordingly, as firing trigger 20 is moved distally, pusher link 74 is moved distally in the direction indicated by arrow "N" in FIG. 52 to effect advancement of pusher back 186 within shell assembly 31 (FIG. 52). Fingers 190 of pusher back 186 engage and eject staples 230 from staple guide 192.

Figure 56:
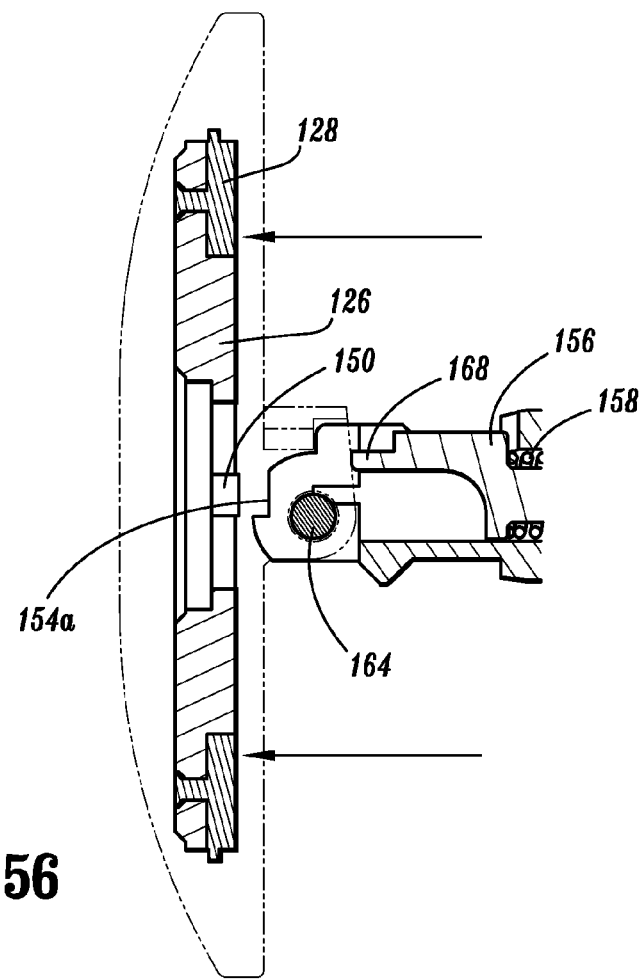
FIG. 56 is a side cross-sectional view of the distal portion of the anvil assembly shown in FIG. 55 with a portion of the anvil head assembly in phantom.
Figure 57:
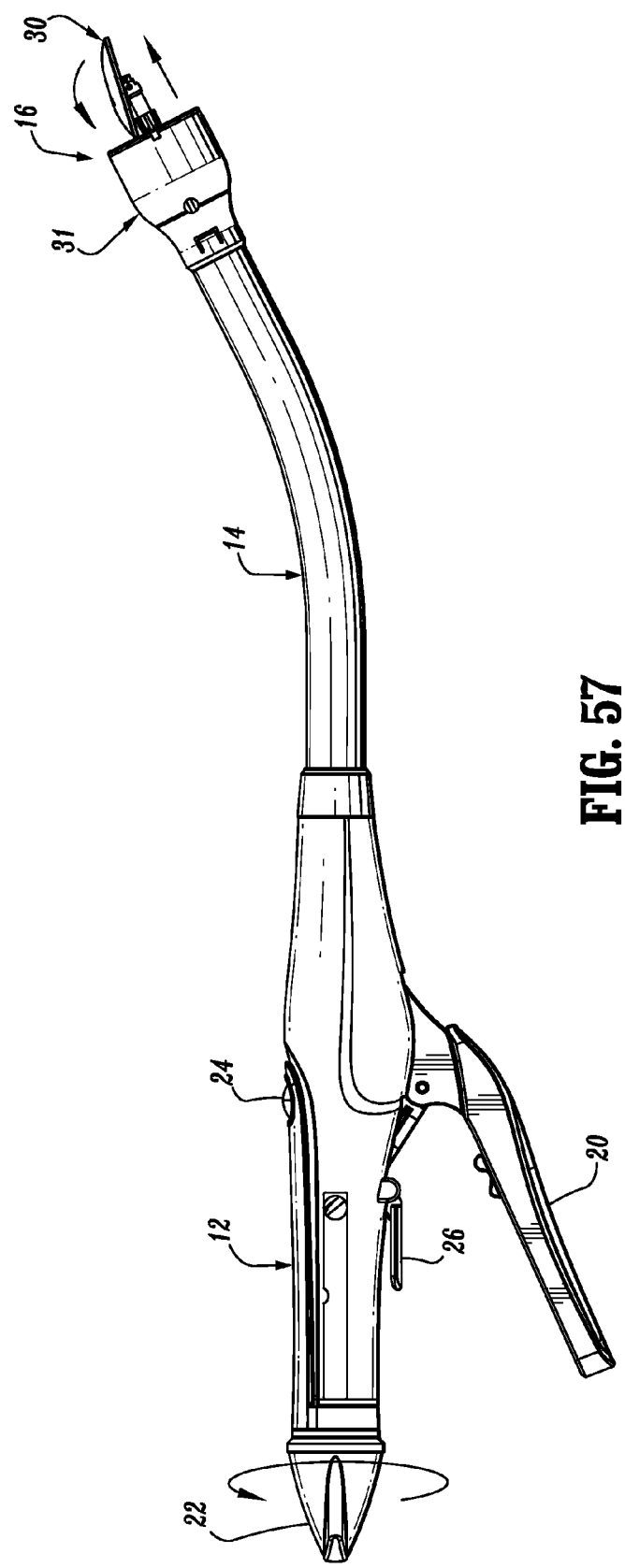
FIG. 57 is a side view of the surgical stapling device shown in FIG. 45 after the anvil assembly and cartridge assembly have been unapproximated a distance sufficient to permit the anvil head assembly to pivot on the anvil center rod.
Figure 59:
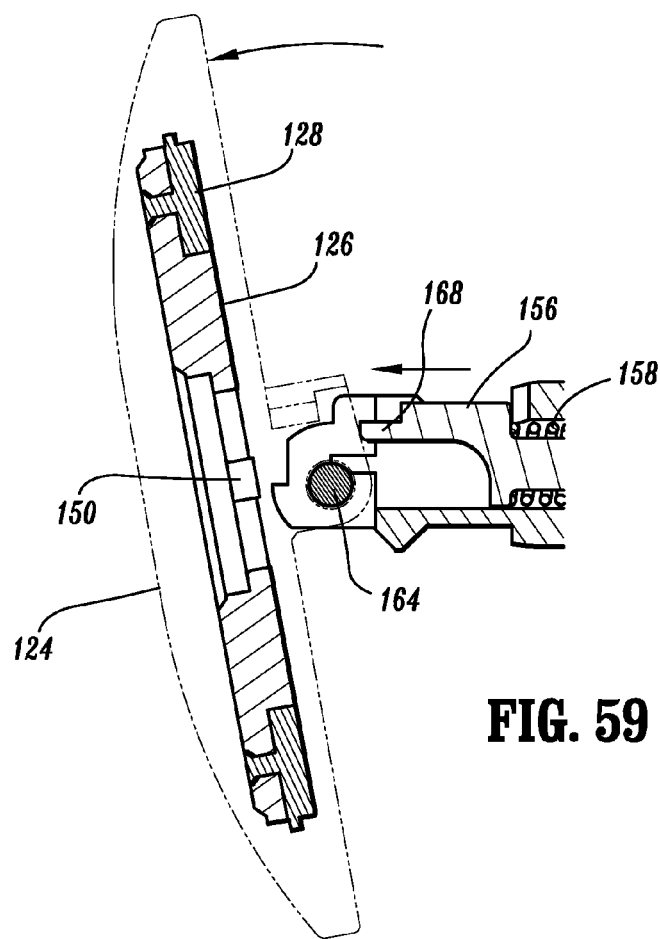
FIG. 59 is a side cross-sectional view of the anvil assembly shown in FIG. 56 as the anvil head assembly begins to tilt.
Figure 60:
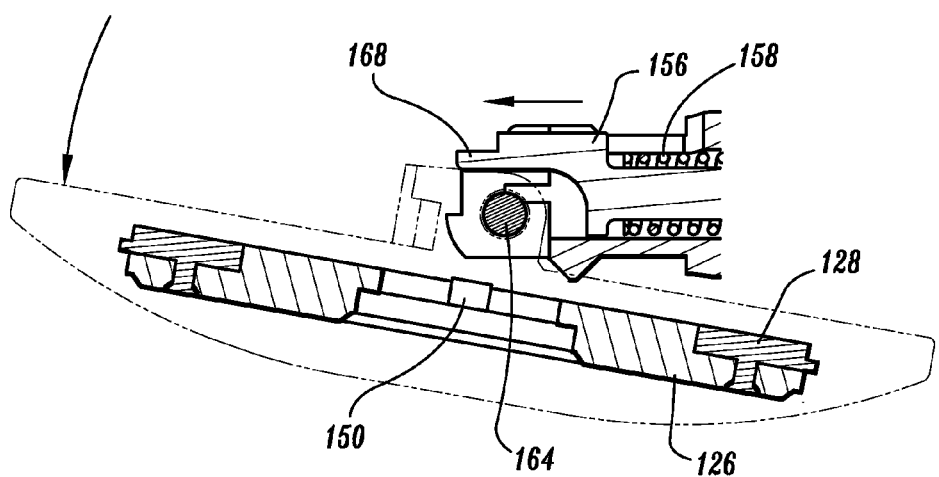
FIG. 60 is a side cross-sectional view of the anvil assembly shown in FIG. 59 with the anvil assembly tilted.
Figure 61:
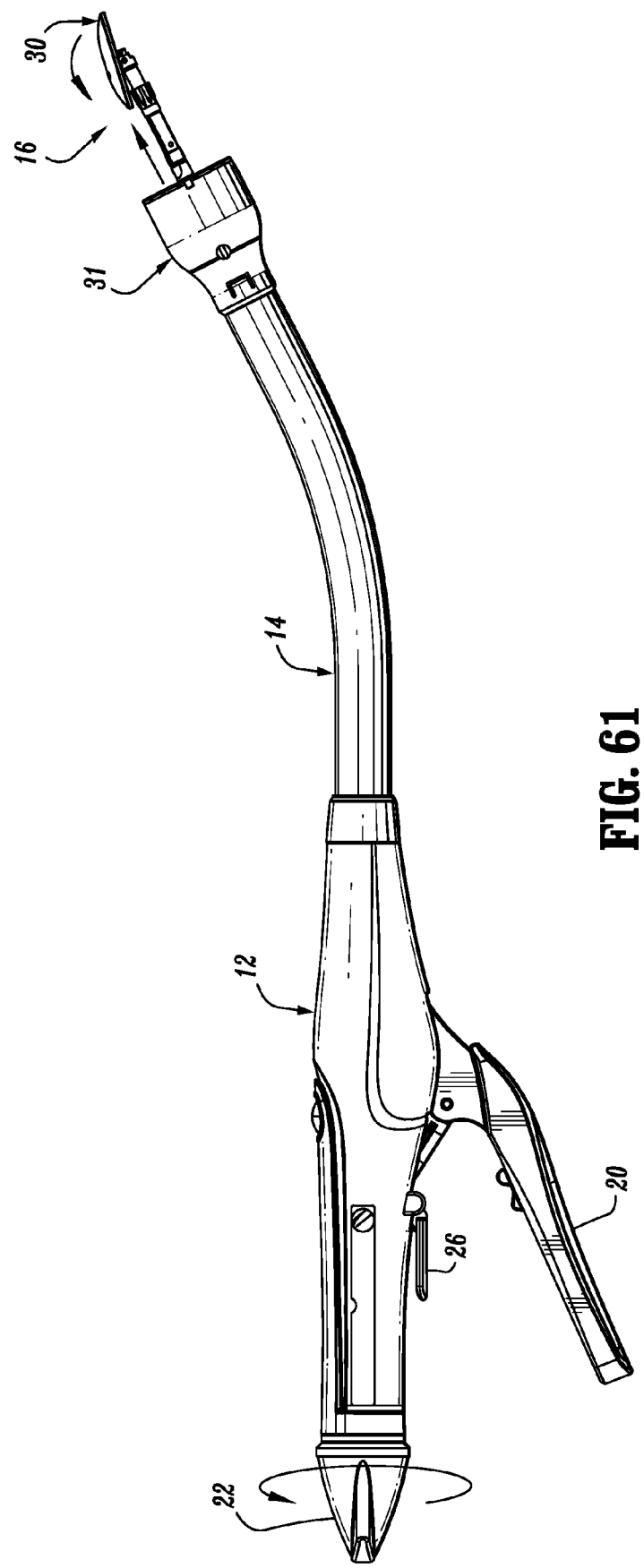
FIG. 61 is a side view of the surgical stapling device shown in FIG. 45 with the anvil head assembly unapproximated and tilted.

Cylindrical knife 188 is moved concurrently with pusher back 186 such that knife 188 moves into engagement with cutting ring 128 and backup plate 126. As discussed above, cutting ring 128 is preferably formed from polyethylene and backup plate 126 is preferably formed from metal. When knife 188 engages cutting ring 128, it cuts into cutting ring 128 and pushes backup plate 126 deeper into anvil head 124 to move tabs 150 (FIG. 56) from engagement with top surface 154a of center rod 154 (FIG. 56). Anvil head 124 is now free to pivot about member 164 and is urged to do so by plunger 156. It is noted that because the anvil assembly is in juxtaposed alignment with shell assembly 31, the anvil head 14 will not pivot fully until the anvil and shell assemblies have been unapproximated a distance sufficient to allow the anvil head to fully pivot. When backup plate 126 moves into anvil head 124, flexible arms 127a and 127b of retainer clip 127 (FIG. 55) spring outwardly to a position in front of backup plate 126 blocking movement of backup plate 126 out of anvil head 124. As discussed above, arms 127a and 127b prevent backup plate 126 from sticking to knife 188 when anvil assembly 30 is returned to the unapproximated position.

Figure 53:
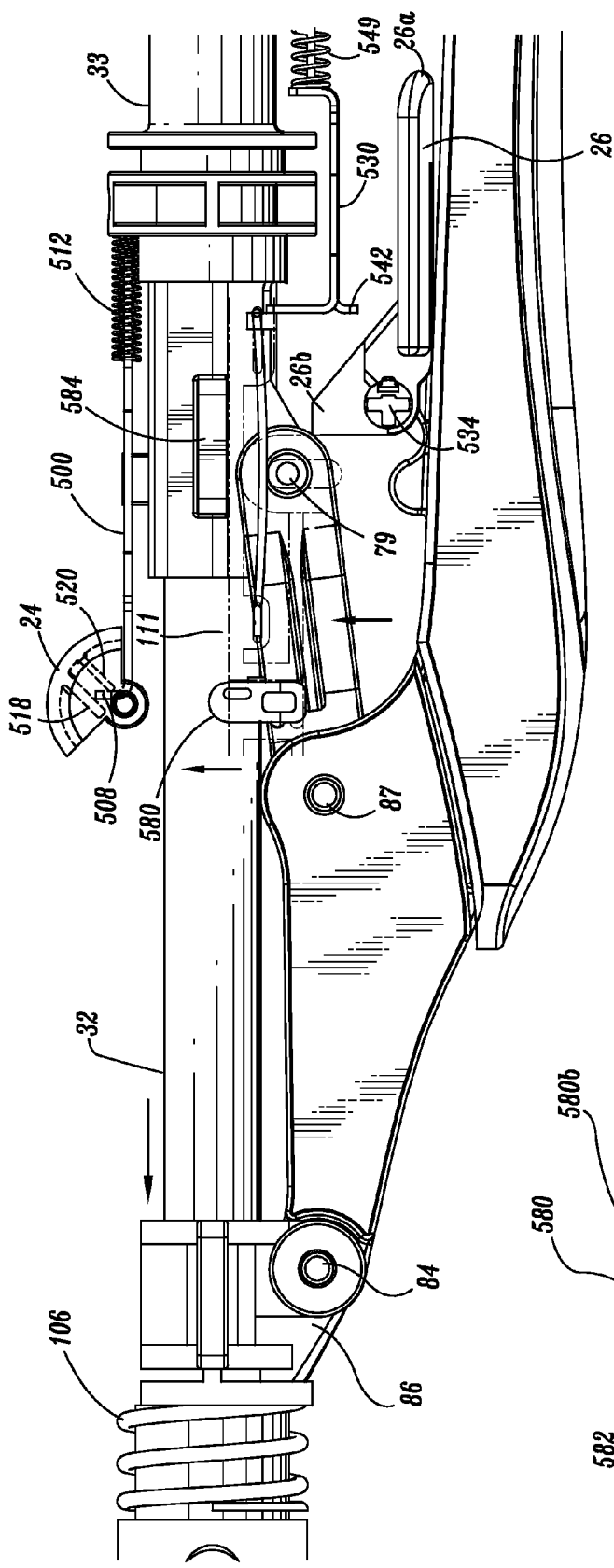
FIG. 53 is a side view of the handle assembly shown in FIG. 51 with the handle sections removed.
Figure 58:
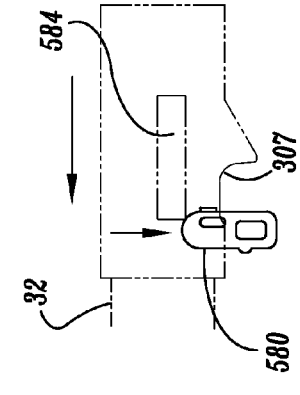
FIG. 58 is an enlarged view of the abutment member of the tactile indicator mechanism of the handle assembly shown in FIG. 53 (during unapproximation of the anvil and cartridge assemblies) with the wing of the screw stop, shown in phantom, in engagement with the abutment member.
Figure 54:
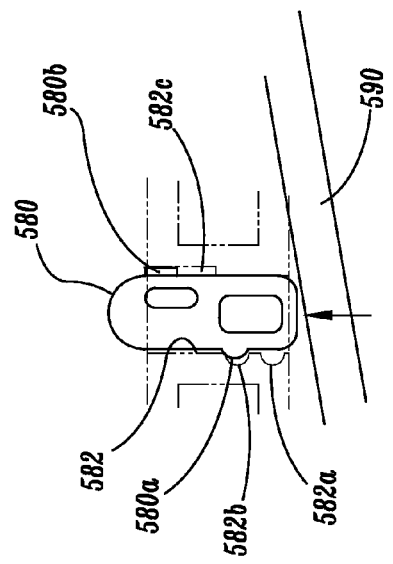
FIG. 54 is an enlarged view of the firing link extension engaging the abutment member of the tactile indicator mechanism of the handle assembly shown in FIG. 53.
Figure 55:
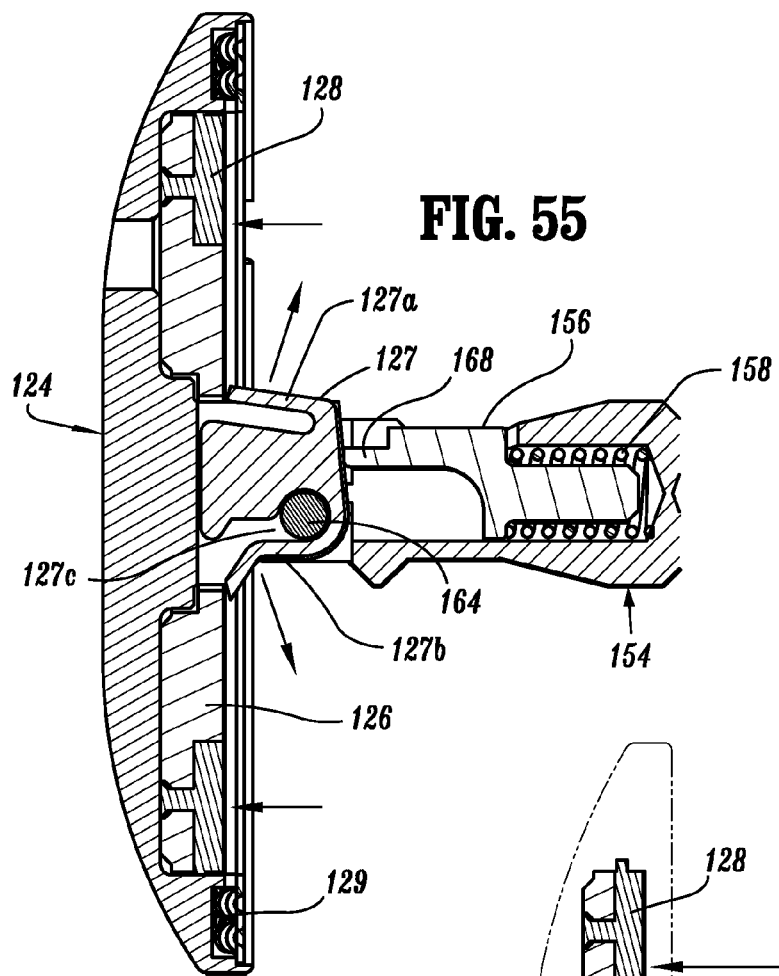
FIG. 55 is a side cross-sectional view of the distal portion of the anvil assembly of the surgical stapling device shown in FIG. 52.

Referring to FIGS. 53 and 54, as trigger 20 is actuated, i.e., compressed towards stationary handle 18, extension 590 of firing link 72 is pivoted towards and engages abutment member 580 to move abutment member 580 from its retracted to its extended position. In its extended position, abutment member obstructs channel 111 of stationary handle 18.

Referring to FIGS. 57-60, during unapproximation of stapling device 10 after device 10 has been fired, wing 584 of screw stop 306 engages tactile indicator 580 (FIG. 58) at the point of unapproximation at which anvil head 124 is able to pivot to the tilted reduced profile position. Contact between wing 584 and tactile indicator 580 provides a tactile and/or audible indication that anvil head 124 has tilted. If additional force is provided to approximation knob 22, wing 584 of screw stop 306 will force tactile indicator to the retracted position to allow stapling device 10 to move to the fully open position. In this position, flexible arms 155 are positioned distally of bushing 209 and anvil assembly 30 can be disengaged from anvil retainer 28.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto. For example, although the description refers exclusively to staples, it is envisioned that staples may include different types of tissue fasteners including two-part fasteners. In a stapling device for applying two-part fastener, the anvil assembly of the stapling device would support one part of each two-part fastener.

What is claimed is:

1. A surgical stapling device comprising:
    a handle portion;
    a body portion;
    a head portion including an anvil assembly and a shell assembly;
    an approximation mechanism including an approximation knob, a drive screw and an anvil retainer, the anvil retainer being operably connected to the drive screw, the drive screw including a helical channel having a first pitch, wherein the approximation knob is operably connected to a pin which is positioned within the helical channel such that rotation of the approximation knob effects linear movement of the anvil retainer between a first advanced position and a second retracted position;
    wherein the anvil assembly includes an anvil center rod configured to releasably engage the anvil retainer, the approximation mechanism being operable to retract engaged portions of the anvil center rod and the anvil retainer within the shell assembly to lock the anvil center rod to the anvil retainer; and
    wherein the helical channel of the screw includes a dwell portion, the dwell portion of the helical channel having a second pitch which is smaller than the first pitch, the dwell portion being positioned along the helical channel to provide a tactile indication to a surgeon that the anvil retainer has been advanced to a third position between the first advanced position and the second retracted position, wherein in the third position, the engaged portions of the anvil center rod and anvil retainer have been advanced from the shell assembly to a position to unlock the anvil center rod and the anvil retainer.

2. A surgical stapling device according to claim 1, wherein the anvil center rod includes a plurality of flexible arms which are positioned to flex over and engage an annular protrusion formed about the anvil retainer.

3. A surgical stapling device according to claim 2, wherein the shell assembly includes an inner guide portion having a rigid bushing dimensioned to slidably receive the engaged portions of the anvil center rod and the anvil retainer, the rigid bushing providing lateral support for the flexible arms of the anvil center rod to prevent disengagement of the anvil center rod from the anvil retainer.

4. A surgical stapling device according to claim 3, wherein the dwell portion of the helical channel is dimensioned to permit between about ½ to about ¾ of a turn of the approximation knob without effecting substantially any linear movement of the screw.

5. A surgical stapling device according to claim 1, wherein the dwell portion of the helical channel is dimensioned to permit between about ½ to about ¾ of the turn of the approximation knob without effecting substantially any linear movement of the screw.

6. A surgical stapling device according to claim 1, further including a pivotable trigger lock supported on the handle portion, the pivotable trigger lock being movable from a first position to prevent actuation of a firing trigger to a second position to permit actuation of the firing trigger.

7. A surgical stapling device according to claim 6, wherein the firing trigger includes a pivotable member.

8. A surgical stapling device according to claim 7, wherein the pivotable member includes first and second spaced abutments, a tip of the pivotable trigger lock being positioned between the spaced abutments when the pivotable trigger lock is in its first position.

9. A surgical stapling device according to claim 8, wherein the tip of the pivotable trigger lock includes a flexible tab which is positioned to engage the pivotable member between the spaced abutments to prevent rattling of the pivotable trigger between the spaced abutments.

10. A surgical stapling device comprising:
a handle portion;
a body portion having a proximal end and a distal end;
a head portion including an anvil assembly and a shell assembly; and
an approximation mechanism including an approximation knob, a drive screw and an anvil retainer, the anvil retainer being operably connected to the drive screw, the drive screw including a helical channel having a first portion defining a first pitch and a dwell portion defining a second smaller pitch, the dwell portion being positioned proximally of the first portion of the helical channel, wherein the approximation knob is operably connected to a pin which is positioned within the helical channel such that rotation of the approximation knob effects linear movement of the anvil retainer between a first advanced position and a second retracted position to move the anvil assembly.

11. A surgical stapling device according to claim 10, wherein the helical channel includes a third portion defining a third pitch which is greater than the first pitch, the third portion of the helical channel being positioned proximally of the dwell portion on the drive screw.

12. A surgical stapling device according to claim 10, wherein the dwell portion is positioned at a location along the helical channel such that, when the pin is positioned within the dwell portion, an indication is provided to a surgeon of a state of the locking arrangement of the anvil retainer and an anvil assembly of the surgical stapling device.

13. A surgical stapling device according to claim 12, wherein the dwell portion of the helical channel is positioned to indicate to a surgeon that the anvil retainer and the anvil assembly are in an unlocked state.

14. A surgical stapling device according to claim 10, wherein the dwell portion is positioned at a location along the helical channel such that, when the pin is positioned within the dwell portion, an indication is provided to a surgeon that the anvil retainer has been advanced a sufficient distance to permit tilting of an anvil head of an anvil assembly attached to the anvil retainer.

15. An approximation mechanism for a surgical stapling device, the approximation mechanism comprising:
an approximation knob, a drive screw and an anvil retainer, the anvil retainer being operably connected to the drive screw, the drive screw including a helical channel having a first portion having a first pitch, wherein the approximation knob is operably connected to a pin which is positioned within the helical channel such that rotation of the approximation knob effects linear movement of the anvil retainer between a first advanced position and a second retracted position, the anvil retainer being releasably connected to a center rod of an anvil assembly, the approximation mechanism being operable to retract engaged portions of the anvil center rod and the anvil retainer into a housing of a surgical stapling device to lock the anvil center rod to the anvil retainer; and
wherein the helical channel of the screw includes a dwell portion, the dwell portion of the helical channel having a second pitch which is smaller than the first pitch such that actuation of the approximation member does not cause substantial linear movement of the anvil retainer when the pin is positioned in the dwell portion, the dwell portion being positioned along the helical channel proximally of the first portion to provide a tactile indication to a surgeon that the anvil retainer has been advanced to a third position between the first advanced position and the second retracted position.

16. The approximation mechanism according to claim 15, wherein the first portion of the helical channel is contiguous with a first end of the dwell portion and a third portion of the helical channel having a third pitch is contiguous with a second opposing end of the dwell portion.

17. The approximation mechanism according to claim 16, wherein the third pitch is greater than the first pitch.

18. A method of approximating an anvil of a surgical stapling device, the method comprising the following steps:
i) providing a surgical stapling device having an approximation mechanism including an anvil retainer and a tactile indicator associated with the approximation mechanism, the tactile indicator indicating to the surgeon that the anvil retainer of the surgical stapling device has been moved to an intermediate position between an advanced position and a retracted position with respect to a stapling head of the instrument;
ii) inserting a distal portion of the surgical device into a body lumen;
iii) performing a surgical stapling procedure;
iv) rotating the approximation knob to move the anvil retainer from the retracted position towards the advanced position, wherein the tactile indicator is positioned on the approximation mechanism to provide an indication to a surgeon of one of the following conditions:
a) the anvil retainer has been moved towards the advanced position a sufficient distance to permit pivoting of an anvil head of an anvil assembly supported on the anvil retainer; and
b) the anvil retainer has been moved towards the advanced position a sufficient distance to unlock the anvil assembly from the anvil retainer to facilitate removal of the anvil assembly from the anvil retainer; and
v) removing the surgical stapling device from the body lumen when the anvil retainer has been moved to the intermediate position.

19. A method according to claim 18, wherein in the intermediate position, the anvil retainer has been moved towards the advanced position a sufficient distance to permit pivoting of an anvil head of an anvil assembly supported on the anvil retainer.

20. A method according to claim 18, wherein in the intermediate position, the anvil retainer has been moved towards the advanced position a sufficient distance to unlock an anvil assembly from the anvil retainer to facilitate removal of the anvil assembly from the anvil center rod.

* * * * *